United States Patent
Kozyak et al.

(10) Patent No.: US 9,849,006 B2
(45) Date of Patent: Dec. 26, 2017

(54) METHODS AND APPARATUSES FOR TREATING VESSELS

(71) Applicant: Children's Medical Center Corporation, Boston, MA (US)

(72) Inventors: Benjamin W. Kozyak, Jamaica Plain, MA (US); James E. Lock, Chestnut Hill, MA (US)

(73) Assignee: Children's Medical Center Corporation, Boston, MA (US)

( * ) Notice: Subject to any disclaimer, the term of this patent is extended or adjusted under 35 U.S.C. 154(b) by 0 days.

(21) Appl. No.: 14/773,899

(22) PCT Filed: Mar. 10, 2014

(86) PCT No.: PCT/US2014/022626
§ 371 (c)(1),
(2) Date: Sep. 9, 2015

(87) PCT Pub. No.: WO2014/150223
PCT Pub. Date: Sep. 25, 2014

(65) Prior Publication Data
US 2016/0015533 A1  Jan. 21, 2016

Related U.S. Application Data

(60) Provisional application No. 61/790,678, filed on Mar. 15, 2013.

(51) Int. Cl.
*A61F 2/07* (2013.01)
*A61F 2/82* (2013.01)
(Continued)

(52) U.S. Cl.
CPC ............... *A61F 2/82* (2013.01); *A61F 2/848* (2013.01); *A61F 2/90* (2013.01); *A61F 2/24* (2013.01);
(Continued)

(58) Field of Classification Search
CPC ...... A61F 2/82; A61F 2/24; A61F 2/06; A61F 2/07
(Continued)

(56) References Cited

U.S. PATENT DOCUMENTS 5,207,695 A   5/1993   Trout, III
5,741,333 A   4/1998   Frid
(Continued)

FOREIGN PATENT DOCUMENTS

WO   WO 2014/150223   9/2014

OTHER PUBLICATIONS

International Search Report and Written Opinion for PCT/US2014/022626 dated Jul. 1, 2014.
(Continued)

*Primary Examiner* — Suzette J Gherbi
(74) *Attorney, Agent, or Firm* — Wolf, Greenfield & Sacks, P.C.

(57) ABSTRACT

Methods and apparatuses relate to treating vessels that have developed an aneurysm or vessels that are expected to develop an aneurysm (e.g., aortic aneurysm). The device may include a conduit having one or more coupling members that serve to couple the conduit and the vessel together. The conduit and coupling member(s) may cooperate to apply an inward radial force (e.g., physical pulling of the vessel wall inward) on the vessel wall, substantially preventing vessel enlargement. In some embodiments, coupling members are disposed at a midpoint region between opposite ends of the conduit, such as regularly along the length of the conduit. When deployed, the device reduces the risk of excessive vessel enlargement which may otherwise lead to undesirable rupture or dissection of the vessel.

23 Claims, 17 Drawing Sheets

(51) Int. Cl.
A61F 2/848 (2013.01)
A61F 2/90 (2013.01)
A61F 2/24 (2006.01)

(52) U.S. Cl.
CPC .............. A61F 2002/8483 (2013.01); A61F 2002/8486 (2013.01); A61F 2230/0067 (2013.01); A61F 2230/0078 (2013.01); A61F 2250/0069 (2013.01)

(58) Field of Classification Search
USPC ............................................. 623/1.15–2.19
See application file for complete search history.

(56) References Cited

U.S. PATENT DOCUMENTS

| | | | | |
|---|---|---|---|---|
| 6,709,455 | B1* | 3/2004 | Chouinard | A61F 2/07 623/1.13 |
| 6,712,843 | B2* | 3/2004 | Elliott | A61F 2/90 623/1.15 |
| 2004/0117003 | A1 | 6/2004 | Ouriel et al. | |
| 2004/0186556 | A1* | 9/2004 | Hogendijk | A61F 2/88 623/1.16 |
| 2006/0106406 | A1 | 5/2006 | Weinberger | |
| 2008/0194905 | A1 | 8/2008 | Walsh | |
| 2008/0262604 | A1 | 10/2008 | Stengel | |
| 2009/0105812 | A1 | 4/2009 | Levin et al. | |
| 2009/0270965 | A1 | 10/2009 | Sinha et al. | |
| 2010/0312330 | A1 | 12/2010 | Majercak et al. | |
| 2011/0238154 | A1* | 9/2011 | Murphy | A61B 17/32072 623/1.15 |
| 2012/0035708 | A1* | 2/2012 | Paul, Jr. | A61F 2/07 623/1.16 |
| 2012/0046733 | A1* | 2/2012 | von Oepen | A61F 2/915 623/1.24 |
| 2013/0289706 | A1* | 10/2013 | Schaeffer | A61F 2/2418 623/1.16 |
| 2014/0005778 | A1* | 1/2014 | Buchbinder | A61F 2/2445 623/2.18 |

OTHER PUBLICATIONS

International Preliminary Report on Patentability for PCT/US2014/022626 dated Sep. 24, 2015.
[No Author Listed], Global Industry Analysts, I., MCP-3226: Ostomy and Incontinence Products—A Global Strategic Business Report (Abstract). 2010. http://www.strategyr.com/Ostomy_And_Incontinence_Products_Market_Report.asp# [Last Accessed Feb. 25, 2016]. 1 page.
[No Author Listed], Grupo Cardiva. BioValsalva. http://www.cardiva.com/en/productos/division-cirugia-cardiaca/recambio-valvular-aortico/products/117 [Last Accessed Oct. 31, 2011]. 4 pages.
[No Author Listed], Research and Markets: Nephrology and Urology Devices Market to 2017—Usage of Incontinence Devices by the Elderly Population to Drive Market. May 25, 2011. http://mobile.reuters. co m/article/2011/05/25/idUS216733+25-May-2011+BW20110525. [Last accessed Feb. 25, 2016]. 3 pages.
[No Author Listed], MarketStrat, I. Nephrology and Urology Devices Market to 2017—Usage of Incontinence devices by the Elderly Population to Drive Market. 2010. Available from and last accessed Mar. 22, 2016: https://leaddiscovery.co.uk/reports/1864/Nephrology_and_Urology_Devices_Market_to_2017_Usage_of_Incontinence_devices_by_the_Elderly_Population_to_Drive_Market. 10 pages.
[No Author Listed], St. Jude Medical. Valved Grafts. http://www.sjmprofessional.com/products/us/heart-valve-eplacement/valved-grafts.aspx [Last Accessed Oct. 7, 2011]. 3 pages.
Badiu et al., Are bicuspid aortic valves a limitation for aortic valve repair? Eur J Cardiothorac Surg. Nov. 2011;40(5):1097-104. doi: 10.1016/j.ejcts.2011.02.008. Epub Mar. 21, 2011.
Badiu et al., Should root replacement with aortic valve-sparing be offered to patients with bicuspid valves or severe aortic regurgitation? Eur J Cardiothorac Surg. Nov. 2010;38(5):515-22. doi: 10.1016/j.ejcts.2010.03.005. Epub Apr. 18, 2010.
Bakhtiary et al., Modification of the David procedure for reconstruction of incompetent bicuspid aortic valves. Ann Thorac Surg. Dec. 2009;88(6):2047-9. doi:10.1016/j.athoracsur.2009.02.100.
Bouma et al., To operate or not on elderly patients with aortic stenosis: the decision and its consequences. Heart. Aug. 1999;82(2):143-8.
Callewaert et al., Ehlers-Danlos syndromes and Marfan syndrome. Best Pract Res Clin Rheumatol. Mar. 2008;22(1):165-89. doi: 10.1016/j.berh.2007.12.005.
Casselman et al., Intermediate-term durability of bicuspid aortic valve repair for prolapsing leaflet. Eur J Cardiothorac Surg. Mar. 1999;15(3):302-8.
Crawford et al., Prevalence of aortic root dilatation and small aortic roots in valvular aortic stenosis. Am J Cardiol. Jun. 1, 2001;87(11):1311-3.
David et al., An aortic valve-sparing operation for patients with aortic incompetence and aneurysm of the ascending aorta. J Thorac Cardiovasc Surg. Apr. 1992;103(4):617-21; discussion 622.
David et al., Long-term results of aortic valve-sparing operations for aortic root aneurysm. J Thorac Cardiovasc Surg. Aug. 2006;132(2):347-54. Epub Jul. 10, 2006.
Della Corte et al., Echocardiographic anatomy of ascending aorta dilatation: correlations with aortic valve morphology and function. Int J Cardiol. Nov. 18, 2006;113(3):320-6. Epub Jan. 18, 2006.
Della Corte et al., Predictors of ascending aortic dilatation with bicuspid aortic valve: a wide spectrum of disease expression. Eur J Cardiothorac Surg. Mar. 2007;31(3):397-404; discussion 404-5. Epub Jan. 22, 2007.
Diehm et al., Aortic neck dilatation after endovascular abdominal aortic aneurysm repair: a word of caution. J Vasc Surg. Apr. 2008;47(4):886-92. doi: 10.1016/j.jvs.2007.09.041. Epub Jan. 16, 2008.
Dobson, Tensegrity Platforms and Geometric Form Finding in ASTRO 2010 Conference, Canada's Future in Space—A Mission in Collaboration. 2010. Toronto, ON, Canada. pp. 1-6.
Doss et al., Pericardial patch augmentation for repair of incompetent bicuspid aortic valves at midterm. Eur J Cardiothorac Surg. May 2008;33(5):881-4. doi: 10.1016/j.ejcts.2008.01.052. Epub Mar. 14, 2008.
Estrada, Analytical and numerical investigations of form-finding methods for tensegrity structures, in Faculty of Computer Science, Electrical Engineering and Information Technology. 2007, Max-Planck-Institute for Metals Research and University of Stuttgart. 152 pages.
Ferencik et al., Changes in size of ascending aorta and aortic valve function with time in patients with congenitally bicuspid aortic valves. Am J Cardiol. Jul. 1, 2003;92(1):43-6.
Greenhalgh et al., Endovascular repair of abdominal aortic aneurysm. N Engl J Med. Jan. 31, 2008;358(5):494-501. doi: 10.1056/NEJMct0707524.
Greenhalgh et al., Endovascular versus open repair of abdominal aortic aneurysm. N Engl J Med. May 20, 2010;362(20):1863-71. doi: 10.1056/NEJMoa0909305. Epub Apr. 11, 2010.
Hiratzka et al., 2010 ACCF/AHA/AATS/ACR/ASA/SCA/SCAI/SIR/STS/SVM guidelines for the diagnosis and management of patients with Thoracic Aortic Disease: a report of the American College of Cardiology Foundation/American Heart Association Task Force on Practice Guidelines, American Association for Thoracic Surgery, American College of Radiology, American Stroke Association, Society of Cardiovascular Anesthesiologists, Society for Cardiovascular Angiography and Interventions, Society of Interventional Radiology, Society of Thoracic Surgeons, and Society for Vascular Medicine. Circulation. Apr. 6, 2010;121(13):e266-369. doi: 10.1161/CIR.0b013e3181d4739e. Epub Mar. 16, 2010. Erratum in: Circulation. Jul. 27, 2010;122(4):e410.
Hirsch et al., ACC/AHA 2005 Practice Guidelines for the management of patients with peripheral arterial disease (lower extremity, renal, mesenteric, and abdominal aortic): a collaborative report from the American Association for Vascular Surgery/Society for Vascular

(56) References Cited

OTHER PUBLICATIONS

Surgery, Society for Cardiovascular Angiography and Interventions, Society for Vascular Medicine and Biology, Society of Interventional Radiology, and the ACC/AHA Task Force on Practice Guidelines (Writing Committee to Develop Guidelines for the Management of Patients With Peripheral Arterial Disease): endorsed by the American Association of Cardiovascular and Pulmonary Rehabilitation; National Heart, Lung, and Blood Institute; Society for Vascular Nursing; TransAtlantic Inter-Society Consensus; and Vascular Disease Foundation. Circulation. Mar. 21, 2006;113(11):e463-654.

Iung et al., Decision-making in elderly patients with severe aortic stenosis: why are so many denied surgery? Eur Heart J. Dec. 2005;26(24):2714-20. Epub Sep. 1, 2005.

Keane et al., Bicuspid aortic valves are associated with aortic dilatation out of proportion to coexistent valvular lesions. Circulation. Nov. 7, 2000;102(19 Suppl 3):III35-9.

Kolvenbach et al., Endovascular management of ascending aortic pathology. J Vasc Surg. May 2011;53(5):1431-7. doi: 10.1016/j.jvs.2010.10.133. Epub Jan. 26, 2011.

Krankenberg et al., Endovascular repair of ascending aortic aneurysm by transapical approach and periscope technique. J Endovasc Ther. Feb. 2013;20(1):13-7. doi: 10.1583/12-4082.1.

Leon et al., Transcatheter aortic-valve implantation for aortic stenosis in patients who cannot undergo surgery. N Engl J Med. Oct. 21, 2010;363(17):1597-607. doi: 10.1056/NEJMoa1008232. Epub Sep. 22, 2010.

Lindroos et al., Prevalence of aortic valve abnormalities in the elderly: an echocardiographic study of a random population sample. J Am Coll Cardiol. Apr. 1993;21(5):1220-5.

Lu et al., Endovascular repair of ascending aortic dissection: a novel treatment option for patients judged unfit for direct surgical repair. J Am Coll Cardiol. May 7, 2013;61(18):1917-24. doi:.10.1016/j.jacc.2012.08.994. Epub Nov. 1, 2012.

Metcalfe et al., The first endovascular repair of an acute type A dissection using an endograft designed for the ascending aorta. J Vasc Surg. Jan. 2012;55(1):220-2. doi: 10.1016/j.jvs.2011.06.116. Epub Sep. 9, 2011.

Moll et al., Management of abdominal aortic aneurysms clinical practice guidelines of the European society for vascular surgery. Eur J Vasc Endovasc Surg. Jan. 2011;41 Suppl 1:S1-S58. doi: 10.1016/j.ejvs.2010.09.011.

Napoli et al., Evaluation of the proximal aortic neck enlargement following endovascular repair of abdominal aortic aneurysm: 3-years experience. Eur Radiol. Aug. 2003;13(8):1962-71. Epub Apr. 12, 2003.

Sampaio et al., Aortic neck dilation after endovascular abdominal aortic aneurysm repair: should oversizing be blamed? Ann Vasc Surg. May 2006;20(3):338-45. Epub May 19, 2006.

Schenk, Theory and Design of Statically Balanced Tensegrity, in Dept. of Biomechanical Engineering. 2006, Delft University of Technology. 94 pages.

Siu et al., Bicuspid aortic valve disease. J Am Coll Cardiol. Jun. 22, 2010;55(25):2789-800. doi: 10.1016/j.jacc.2009.12.068.

Tzemos et al., Outcomes in adults with bicuspid aortic valves. JAMA. Sep. 17, 2008;300(11):1317-25. doi: 10.1001/jama.300.11.1317.

Varadarajan et al., Clinical profile and natural history of 453 nonsurgically managed patients with severe aortic stenosis. Ann Thorac Surg. Dec. 2006;82(6):2111-5.

Wilton et al., Post-stenotic aortic dilatation. J Cardiothorac Surg. Mar. 3, 2006;1:7.

Yacoub et al., Late results of a valve-preserving operation in patients with aneurysms of the ascending aorta and root. J Thorac Cardiovasc Surg. May 1998;115(5):1080-90.

\* cited by examiner

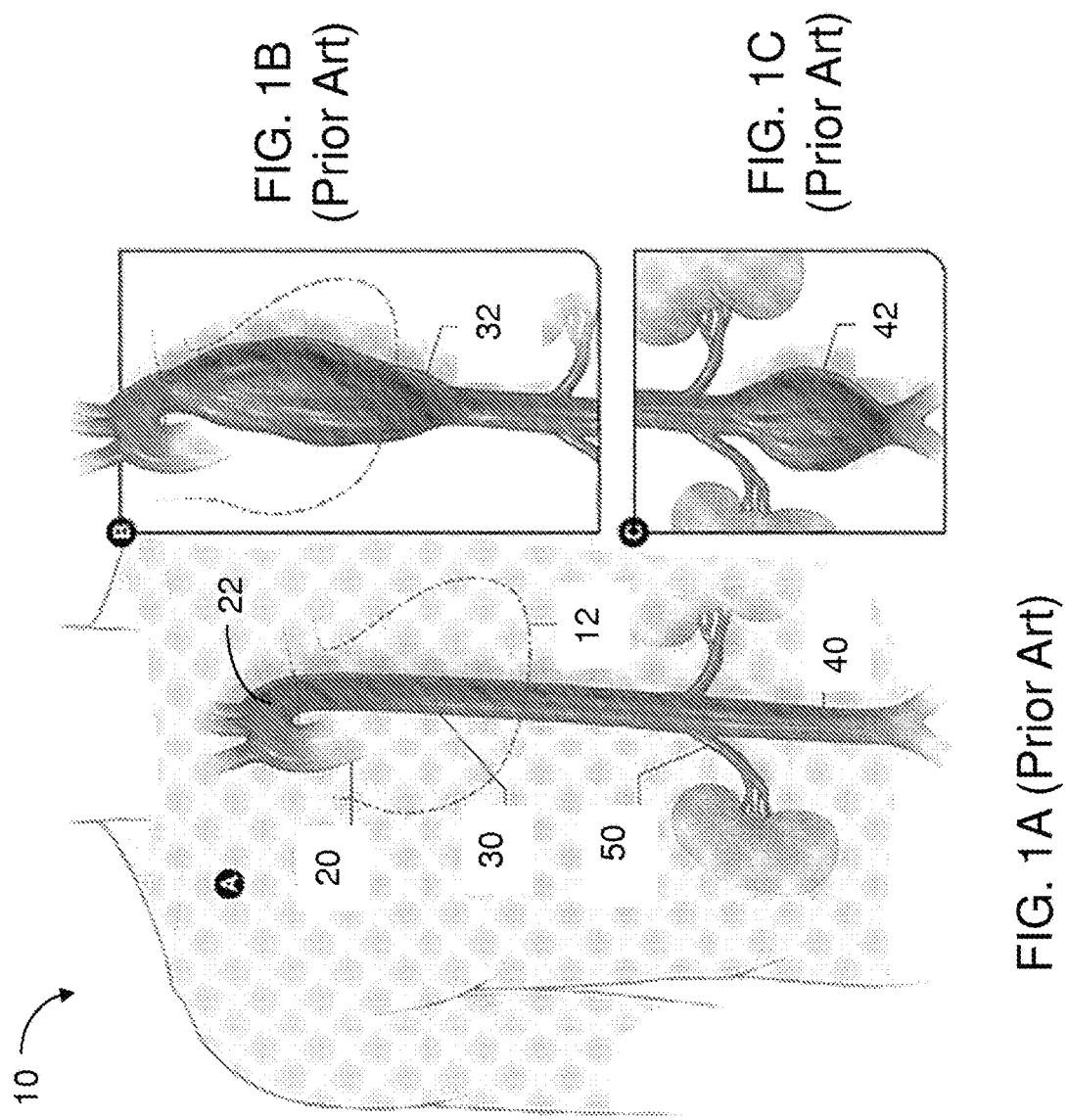

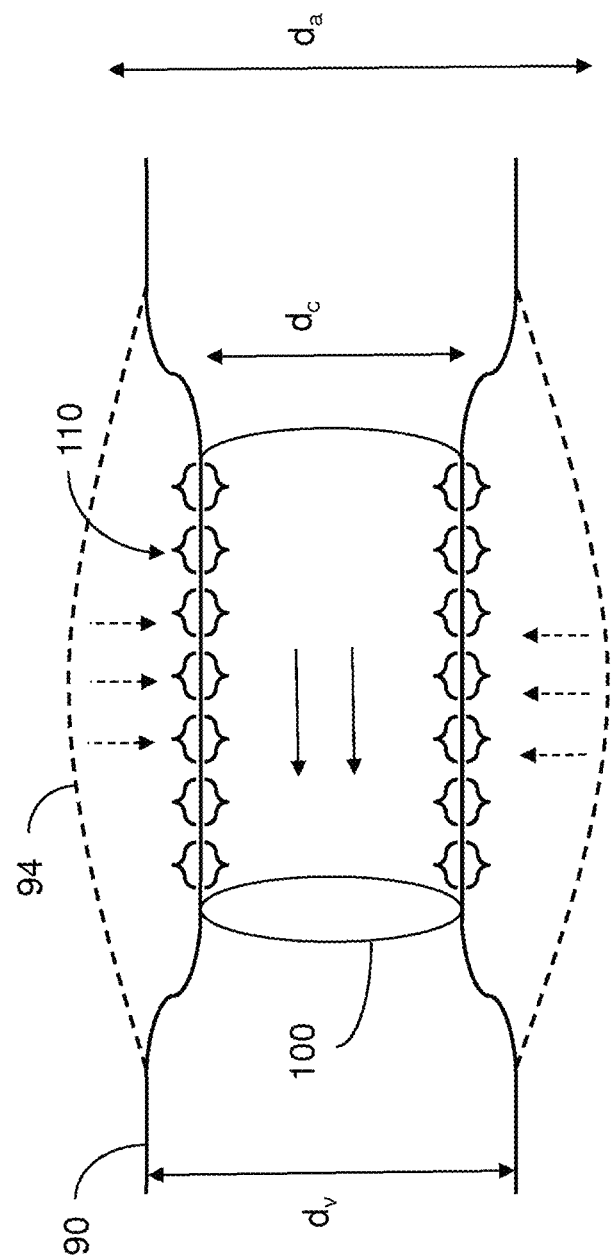

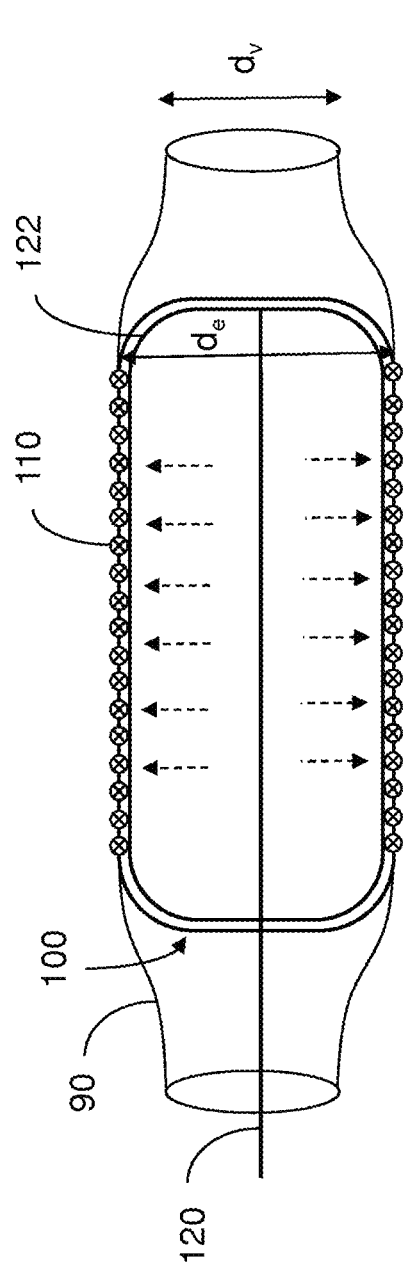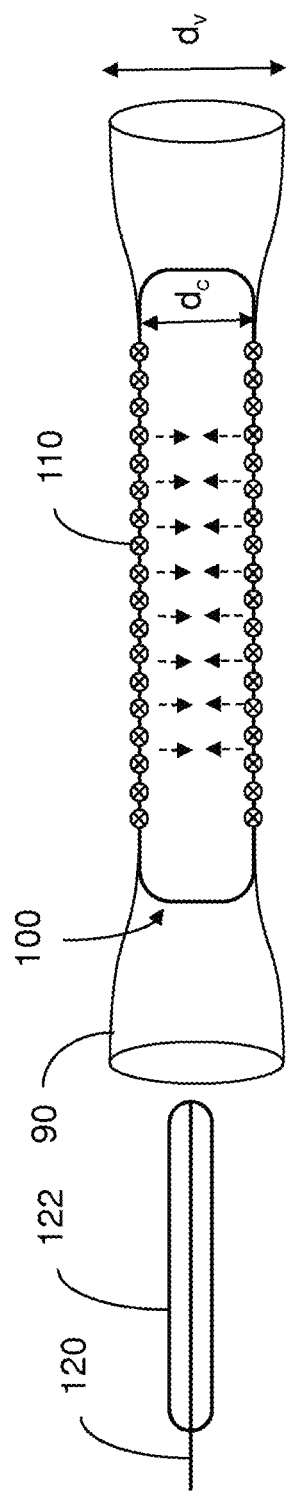
FIG. 6C
FIG. 6D

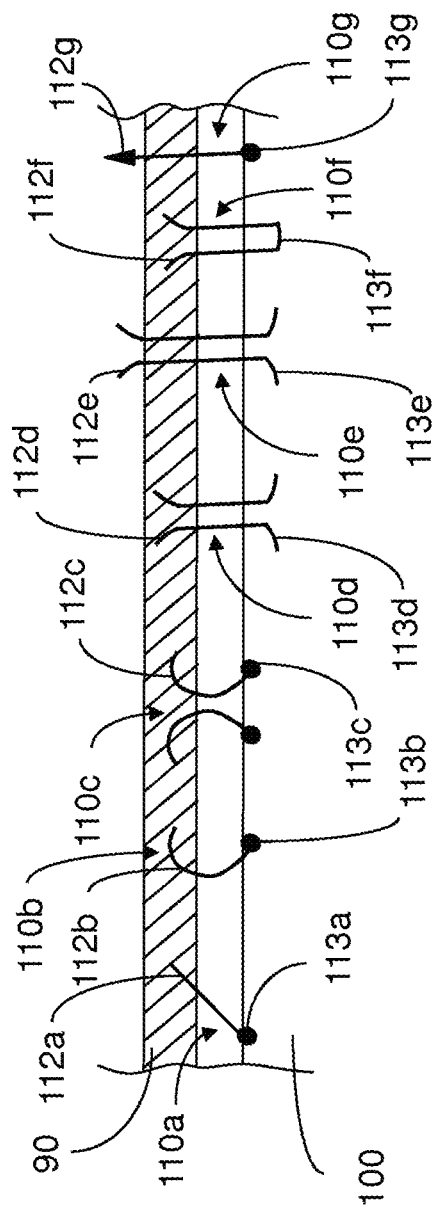
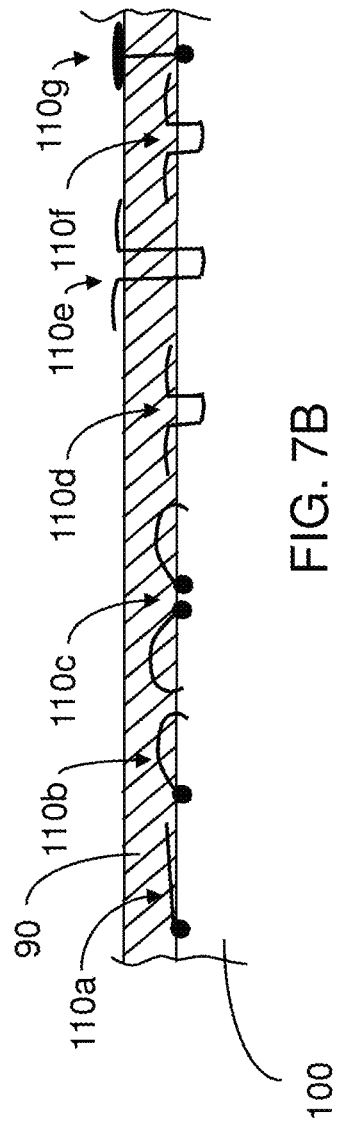
FIG. 7A
FIG. 7B

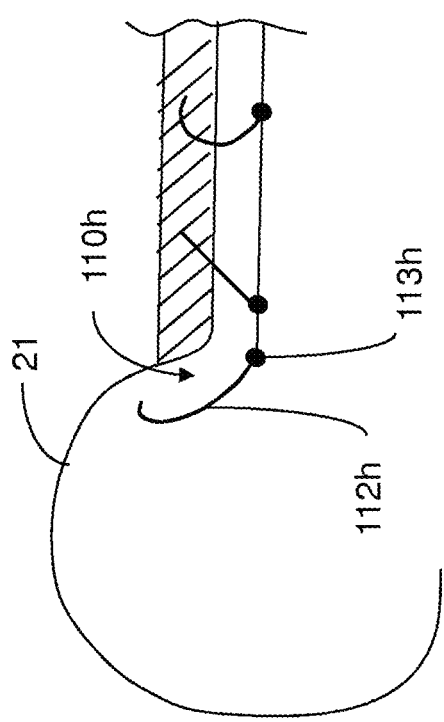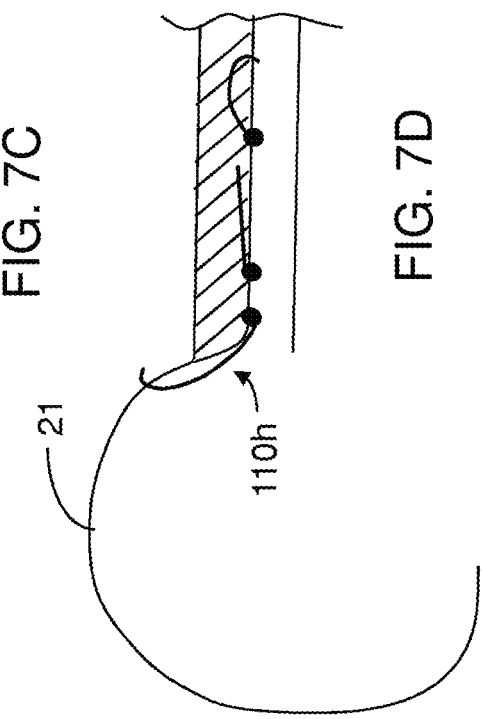

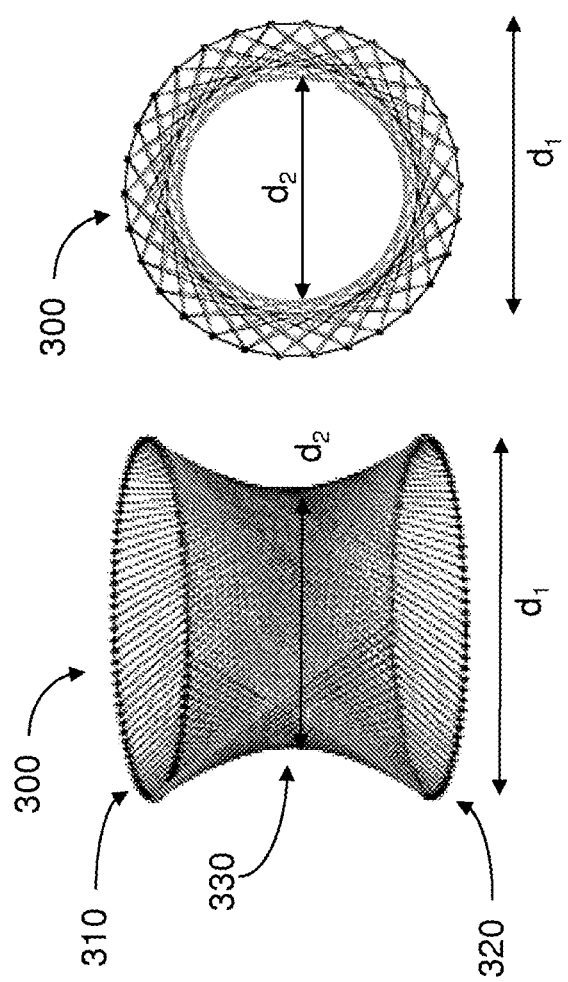

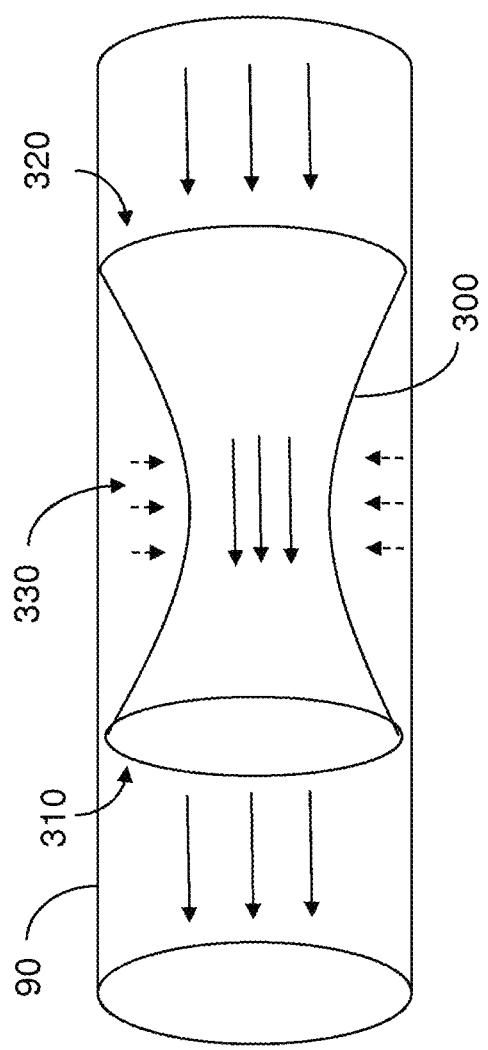

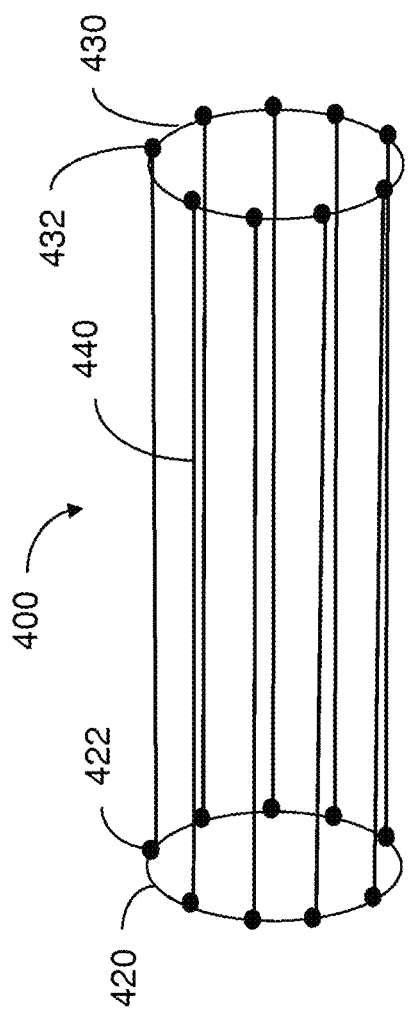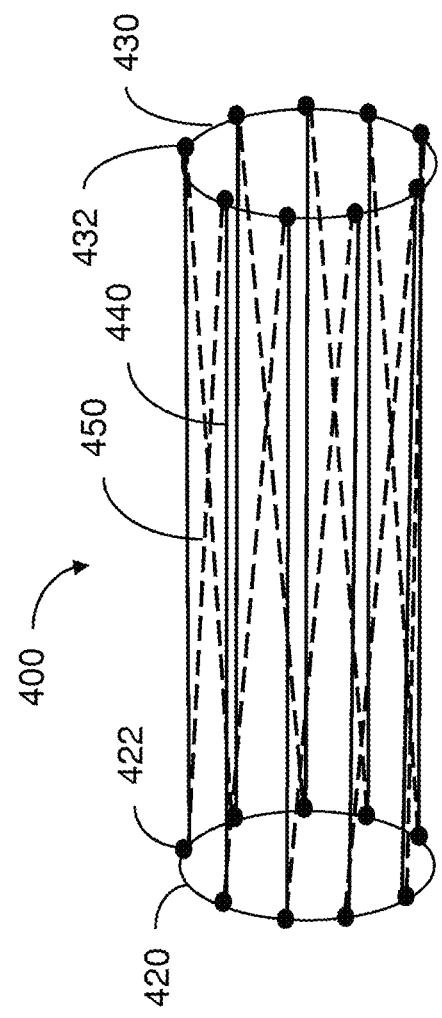

METHODS AND APPARATUSES FOR TREATING VESSELS

RELATED APPLICATIONS

This application is a national stage filing under 35 U.S.C. §371 of international application PCT/US2014/022626 filed Mar. 10, 2014, which claims the benefit under 35 U.S.C. §119(e) of U.S. provisional application serial number 61/790,678, filed Mar. 15, 2013, entitled "METHODS AND APPARATUSES FOR TREATING VESSELS", the contents of which are incorporated by reference in their entireties.

BACKGROUND

1. Field

Aspects of the present disclosure relate to implantable devices and methods for treating a vessel, such as a vessel having an aneurysm (e.g., aortic aneurysm).

2. Discussion of Related Art

Patients suffering from an aneurysm in a vessel are at risk for dissection or rupture of the vessel and potentially death. In general, aneurysms may be characterized by the occurrence of an abnormal swelling or dilation in a region of a blood vessel, typically to an amount greater than 1.5 times that of normal dimensions. Such pathologic dilation of the vessel may arise due to the development of an underlying weakness, or weakening, in the wall of the vessel. For instance, an aneurysm may arise due to abnormal architecture of the vessel wall due to an insufficient amount of load-bearing protein, such as elastin, to support forces (e.g., hydrostatic pressure) within the vessel. These structural defects in cellular or connective tissue may be inherited, as in the case of Marfan syndrome (fibrillin defect), or acquired, as seen in atherosclerotic degeneration. In other cases, the vessel may have an inadequate level of vascularization for the vessel wall to be sufficiently repaired when damaged or worn.

Aortic aneurysms are classified primarily by location, as enlargement may occur anywhere along the length of the aorta. FIG. 1A depicts the inside of a human cavity 10 where blood flow from the heart 12 passes through the ascending aorta 20 and travels through a system of branch vessels leading to supply all parts of the body. FIG. 1A further illustrates the aortic arch 22 arising from the ascending aorta and leading to the descending aorta, which includes the descending thoracic aorta 30 and the abdominal aorta 40, as demarcated by the diaphragm. Renal arteries 50 leading to the kidneys are also illustrated as vessels branching off the abdominal aorta. FIG. 1B depicts dilation in the thoracic aorta 30 giving rise to a thoracic aortic aneurysm 32. Similarly, dilation of the abdominal aorta 40 is shown in FIG. 1C resulting in an abdominal aortic aneurysm 42. FIG. 2A illustrates a heart 12 where an ascending aortic aneurysm 20 has developed in the ascending aorta. In this depiction, the ascending aorta is connected to a healthy aortic root 24. In other situations, the aortic root itself may be diseased or dilated. FIG. 2B illustrates a schematic of sinuses of valsalva 21 shown as cusps of the aortic root located immediately downstream from the valve leaflets.

Aneurysms of the abdominal and descending thoracic aorta are most common; however, many people suffer from abnormal dilation of the ascending aorta, aortic arch, and aortic root as well. For example, patients with connective tissue disorders such as those with Marfan Syndrome are likely to experience abnormal aortic dilation within a typical lifespan. In Marfan patients, abnormal dilation typically begins at the aortic root but may affect other regions of the vessel as well. Similarly, patients with a bicuspid aortic valve (approximately 2% of the population), are known to exhibit abnormal dilation of the ascending aorta, likely due to a connective tissue abnormality. Abnormal aortic dilation, in turn, is a common precursor to aortic dissection or rupture. Disease of the proximal aorta (i.e., ascending aorta and root) is also frequently, although not always, associated with disease of the aortic valve, and such an association may dictate medical management. Currently, treatment of aneurysms of the ascending aorta and arch typically involves complex surgical replacement of the diseased vessel, and often involves simultaneous replacement of an abnormal aortic valve. Such a valve, despite being structurally abnormal, may not exhibit significant dysfunction or otherwise merit replacement at the time of intervention on the dilated vessel, rather the decision may be made by the surgeon to replace it prophylactically at the time of vessel surgery, under the assumption that it will eventually become dysfunctional. This decision is not without consequence, however, as the vascular grafts and bioprosthetic valves used for replacement have a limited life span. More durable, mechanical prosthetic valves require life-long anticoagulation, which also carries significant risk. Therefore, premature replacement of a valve with a prosthesis may subject the patient to risk of bleeding, and/or result in the need for additional, repeat operations of increasing complexity and morbidity over the patient's lifetime. There are few alternatives to these repeat surgical procedures currently available.

SUMMARY

The inventors have recognized and appreciated a growing need to develop improved methods and devices for treating vessels subject to the development of an aneurysm. Methods and devices described herein may be particularly useful for treating various types of aortic aneurysms, such as ascending aortic aneurysms, abdominal aortic aneurysms and thoracic aortic aneurysms. In treating ascending aortic aneurysms, aspects of the present disclosure provide viable alternatives to surgical resection and replacement of the ascending aorta. Suitable methods and devices described herein may be used in any bodily vessel where fluid may flow, such as blood vessels (e.g., arteries, veins, capillaries) or other appropriate bodily vessels (e.g., urethra, intestine, etc.).

In some cases, an implantable device for a vessel includes a conduit configured with one or more coupling members (e.g., hooks, barbs, adhesive material, staples, sutures, etc.) for coupling together at least a portion of the conduit and a vessel wall at an interior region of the vessel. Upon suitable coupling of the conduit and the vessel wall, the coupling member may cooperate with the conduit in a manner that results in an inward radial force exerted on the vessel wall. The device may be implanted within a vessel by any suitable method, such as through a catheter assembly capable of causing expansion of the conduit and assisting an appropriate portion of the conduit to be coupled to the interior of the vessel wall. It may also be implanted surgically. Once the conduit and the vessel wall are suitably coupled (e.g., attached), the conduit can adapt to an equilibrium conformation resulting in pulling of the vessel wall radially inward. In some embodiments, suitable coupling of the conduit and the vessel wall may result in an overall constrictive effect on the vessel. In some embodiments, such an inwardly directed radial force is not large enough to substantially constrain the vessel wall, but may serve to enhance coupling of the conduit to the vessel wall, where any outward directed force applied from the device to the vessel wall is negligible, if at all present.

In some embodiments, upon suitable implantation of the device within a vessel, a coupling member couples the conduit and an interior region of the vessel wall together at a midpoint region of the conduit. The midpoint region may be located anywhere between opposite ends of the conduit. For instance, a number of coupling members may be disposed regularly or irregularly along the majority of the length of the conduit between opposite ends of the conduit for suitably attaching the conduit and the vessel wall to one another. The implantable device may be deployed in a manner such that coupling members located at opposite ends of the conduit and/or along the length of the conduit, for example, at or across a midpoint region between opposite ends of the conduit, couple the conduit with the vessel wall. Upon deployment of the device and associated coupling of the conduit to the vessel wall, an inward radial force may subsequently be exerted on the interior of the vessel wall. For example, the conduit may constrict so as to physically pull the vessel wall inward. In some embodiments, such an inward radial force involves physical pulling of the vessel wall to a position where the diameter of the vessel at certain locations is less than what the diameter of the vessel would be absent the inward radial force. Accordingly, the risk for a vessel to undergo undesirable enlargement or to develop an aneurysm (e.g., ascending aortic aneurysm, abdominal aortic aneurysm, thoracic aortic aneurysm, etc.) may be reduced upon suitable deployment of the device within the vessel.

In an illustrative embodiment, an implantable device for a vessel is provided. The device includes a conduit; and at least one coupling member constructed and arranged to couple a portion of the conduit with a wall region of the vessel at an interior of the vessel, the at least one coupling member cooperating with the conduit resulting in exertion of an inward radial force on the wall region of the vessel. The region of the vessel engaged with the coupling may be at any point along the length of the device. In an embodiment, the device is utilized for the treatment of an aneurysm of the proximal aorta (e.g. aortic root, ascending aorta, aortic arch). In deploying the device in this region, it may couple to the walls of the vessel as described, or may couple to the interior of the vessel, for example, by engaging hooks, or any other such coupling mechanism described, within the sinuses of valsalva in such a way that the coupling elements prevent the device from becoming displaced (e.g., moving downstream from the heart, or upstream toward the aortic valve, undergoing lateral displacement). These particular elements, mounted on one end of the device, may or may not function in the same way as the other coupling elements on the device. For instance, they may or may not serve to exert an inward radial force on the vessel, but rather function to hold the device in place.

In another illustrative embodiment, an implantable device for a vessel is provided. The device includes a conduit having a midpoint region located between a first end portion and a second end portion of the conduit; and at least one coupling member constructed and arranged to couple at least the midpoint region of the conduit with a wall region of the vessel at an interior of the vessel.

In a further illustrative embodiment, a method of treating a vessel is provided. The method includes implanting a device having a conduit within the vessel, coupling a portion of the conduit with a wall region at an interior of the vessel; and providing an inward radial force to the wall region of the vessel at the coupled portion of the conduit.

In yet another illustrative embodiment, a method of treating a vessel is provided. The method includes implanting a device having a conduit within the vessel, the conduit including a midpoint region located between a first end portion and a second end portion of the conduit; and coupling a portion of the conduit with a wall region at an interior of the vessel and at the midpoint region of the conduit.

Various embodiments of the present invention provide certain advantages. Not all embodiments of the invention share the same advantages and those that do may not share them under all circumstances.

Further features and advantages of the present invention, as well as the structure of various embodiments of the present invention are described in detail below with reference to the accompanying drawings.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. Various embodiments of the invention will now be described, by way of example, with reference to the accompanying drawings, in which:

FIG. 1A depicts a schematic diagram of a human aorta within a bodily cavity;

FIG. 1B illustrates a schematic diagram of an aneurysm of the (descending) thoracic aorta;

FIG. 1C shows a schematic diagram of an abdominal aortic aneurysm;

FIG. 5 illustrates a schematic of a device deployed in a vessel in accordance with some embodiments;

FIGS. 6A-6D depict a process for deploying a device in a vessel in accordance with some embodiments;

FIGS. 7A-7B show different coupling members in various configurations in accordance with some embodiments;

FIGS. 7C-7D show coupling members in various configurations at a sinus of valsalva region in accordance with some embodiments;

FIGS. 10A-10B depict schematics of a device in accordance with some embodiments;

FIG. 11 illustrates a schematic of a device deployed in a vessel in accordance with some embodiments;

FIGS. 12A-12C illustrate a device in various configurations in accordance with some embodiments;

DETAILED DESCRIPTION

Figures 2A, 2B:
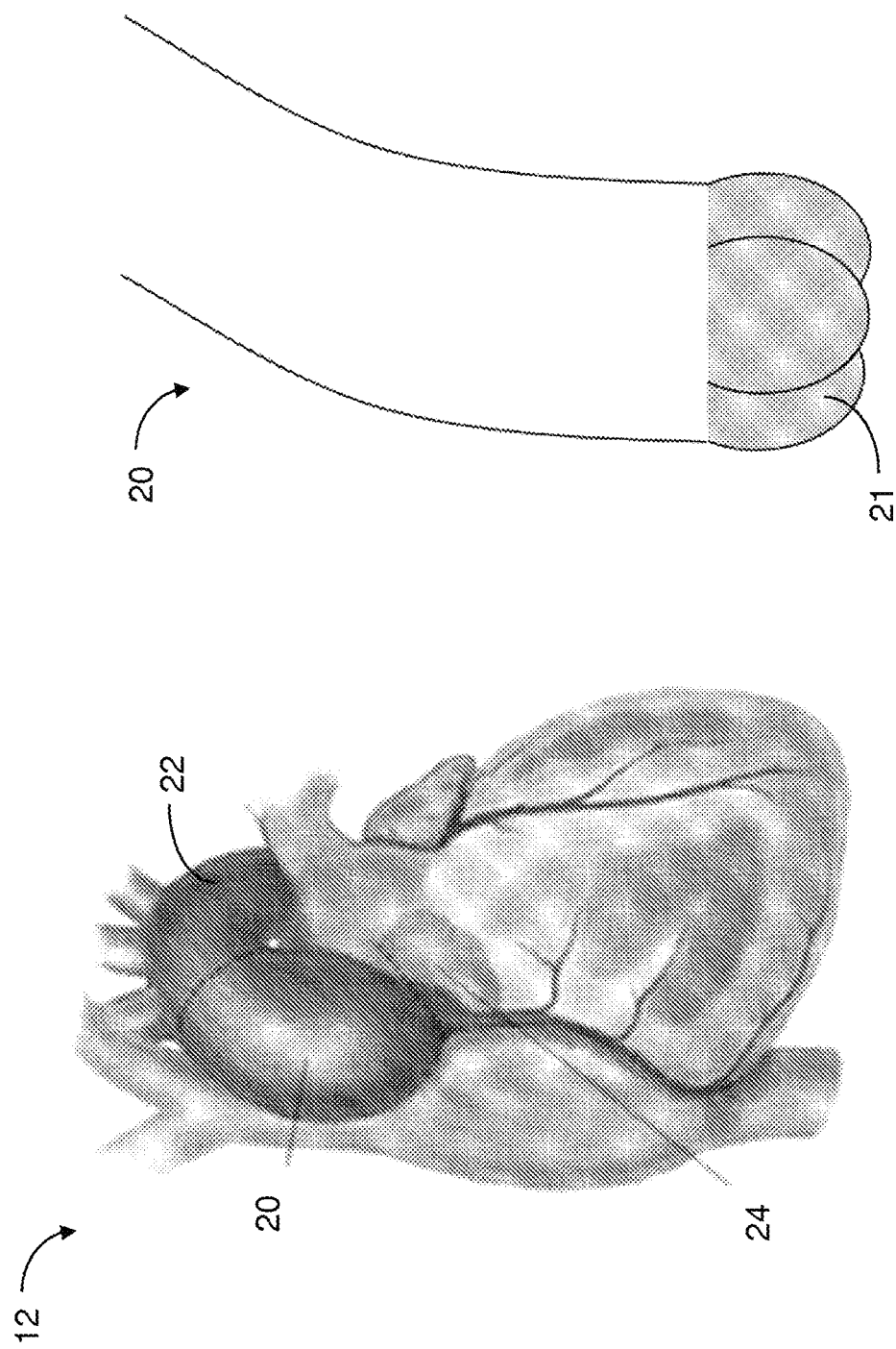
FIG. 2A shows a schematic diagram of a heart and an ascending aortic aneurysm.
FIG. 2B depicts a schematic diagram of sinuses of valsalva and an ascending aorta.

The present disclosure relates to implantable devices and methods for treating vessels having developed an aneurysm or vessels that are at risk for developing an aneurysm. In some embodiments, methods and devices discussed herein are useful for treating aortic aneurysms, for example, aneurysms of the ascending aorta, aortic arch, descending thoracic aorta or abdominal aorta. For instance, a device in accordance with the present disclosure may be deployed in a region of a vessel (e.g., ascending aorta) in which the aneurysm has occurred or that is at risk for development of the aneurysm. In some embodiments, the device includes a conduit having one or more coupling members such that upon deployment of the device in a vessel, the conduit and coupling member(s) suitably engage with the vessel wall and cooperate to apply an inward radial force on the vessel wall. Although, in other embodiments, the conduit and coupling member(s) engage with the vessel wall, yet are not arranged so as to apply such an inward radial force on the vessel wall.

In one embodiment, coupling members are located at a midpoint region between opposite ends of the conduit. In an embodiment, coupling members may be located regularly, or otherwise, along a majority of the length of the conduit. Upon suitable deployment, the device advantageously prevents excessive enlargement of the vessel at the region of deployment. In embodiments described herein, suitable deployment of the device refers to situations where the device is finally implanted at an appropriate location within the body and decoupled from one or more deployment instruments that may have been used to place the device into position.

Accordingly, certain situations where surgical replacement or bypass of the ascending aorta, which would typically be recommended by professional medical personnel, may be averted through use of methods and devices described herein. Rather than having to undergo surgical replacement or bypass (e.g., construction of an alternate route for fluid flow external to the vessel) of the ascending aorta due to risks of excessive dilation and/or rupture of the vessel, for more favorable treatment of the vessel, a suitable device may be implanted within the ascending aorta instead. It can be appreciated that aspects of the present disclosure are not limited to vessels having an aortic aneurysm or vessels having an aneurysm at all. For example, embodiments described may be useful to treat arteries, veins, the urethra, intestines or other appropriate bodily vessels through which fluid may flow.

In some embodiments, an implantable device useful for treating a vessel (e.g., a vessel having an aneurysm, a vessel at risk for developing an aneurysm, etc.) includes a conduit that has a coupling arrangement which may include appropriate coupling members, such as but not limited to, hooks, barbs, adhesive material, staples, sutures, or the like. Coupling members may be used to couple or attach a portion of the conduit and a region of the vessel wall together. In some embodiments, the coupling may occur at an interior of the vessel. For example, the coupling member(s) may be pre-attached to the conduit and, via suitable deployment of the implantable device, an attached arrangement between the conduit and the vessel wall may be established via the coupling member(s).

In cooperation with the conduit, the coupling member may optionally provide for an inward radial force to be exerted on the vessel wall. For instance, a device suitably deployed in a vessel may have a conduit attached to the vessel wall via one or more coupling members. Upon full deployment, the conduit may constrict to an equilibrium conformation leading to the vessel wall being pulled radially inward at attachment sites of the coupling member(s).

The inward radial force provided by the combination of the conduit and/or the coupling member(s) on the vessel wall may involve pulling of the vessel wall radially inward so as to reach a suitable diameter of the vessel at locations where the vessel wall is coupled to the conduit. In this respect, the diameter of the vessel may be the same or similar to the diameter of the conduit at coupled locations while in the deployed configuration. In some embodiments, due to exertion of the inward radial force provided by the conduit and/or the coupling member(s), the vessel at the region where coupling occurs constricts along with the conduit such that a diameter, or width, of the vessel at that region is less than what the diameter of the vessel at that region would normally be (e.g., healthy or with an aneurysm) absent deployment of the implantable device. In some embodiments, the resulting diameter, or width (e.g., diameter/width at equilibrium), of the vessel due to application of the inward radial force on the vessel from the conduit and coupling member(s) substantially aligns with the diameter of the conduit in the deployed configuration. The vessel is effectively held in place to conform with the deployed conduit (e.g., having a smaller more constricted diameter, or diameter that is approximately the same) and coupling member arrangement. Accordingly, when a device according to one or more aspects as described herein is implanted into an appropriate region of a vessel, because of the coupled arrangement between the conduit and the vessel wall, the risk for aneurysm development or further detrimental enlargement in the vessel is reduced.

When fluid (e.g., blood, plasma, other bodily fluids) flows through a vessel, depending on the volume and velocity of fluid flow, the vessel wall may be subject to pressure (e.g., hydrostatic, hydrodynamic). As discussed previously, for a vessel that has developed an aneurysm or a vessel that is at risk for the occurrence of an aneurysm, the tissue region where the walls of the vessel are subject to abnormal dilation are generally weaker in comparison to healthier tissue that surrounds the relatively weaker tissue region. In a number of instances, the likelihood that a vessel will become further enlarged due to build up of stress in the vessel wall increases as the vessel diameter increases. In other words, when a vessel becomes radially enlarged, the tangential stress on the wall increases, resulting in further, progressive dilation and an increasing risk for rupture. As a result, the weakened walls of the vessel subject to an aneurysm may be increasingly prone to greater degrees of dilation due to the applied pressure arising from fluid flow through the vessel.

Methods for treating aortic aneurysms (e.g., abdominal, thoracic) may involve insertion of a device in accordance with embodiments of the present disclosure, such as a covered conduit (e.g., covered stent), in the region of the vessel where the aneurysm has developed. For instance, a deployed covered conduit may make suitable contact with healthy tissue in the vessel disposed on opposite sides of the aneurysm where the healthy tissue is not subject to abnormal enlargement. In some cases, such healthy tissue may be referred to as proximal and distal landing zones. In some embodiments, the covered conduit provides a lumen through which fluid may flow and where an exterior surface of the covered conduit is spaced inwardly from an interior surface of the enlarged vessel wall. Accordingly, fluid passing through the vessel at the region where the aneurysm has occurred may generally be diverted from flowing into the region between the exterior surface of the conduit and the tissue subject to enlargement and, rather, through the lumen provided by the covered conduit. As a result, the abnormally enlarged region of the vessel experiences substantially less fluid flow and lower applied pressure, since the fluid travels predominantly through the lumen of the covered conduit, which possesses its own structural integrity and ability to resist hydrostatic and mechanical forces. Therefore, a smaller amount of pressure is experienced by the abnormally enlarged region of the vessel wall, lessening the likelihood for progressive dilation of the aneurysm to occur.

Figure 3B:
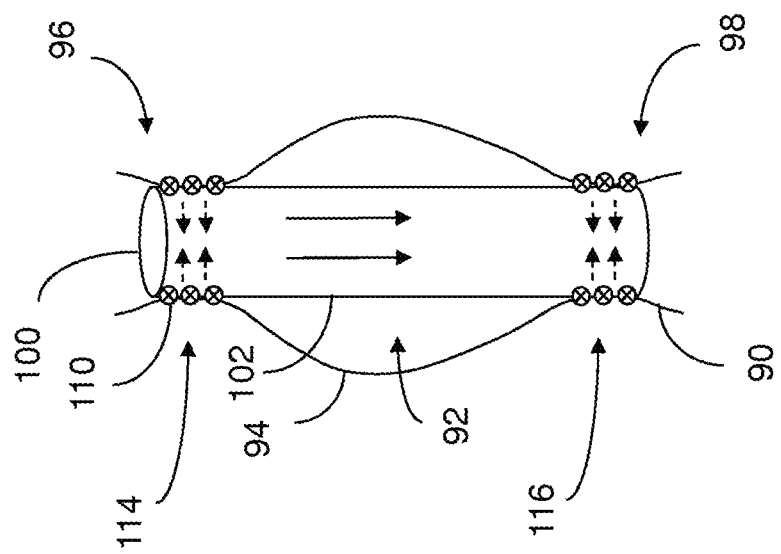
FIGS. 3A-3B depict schematics of treatment methods and devices for an aneurysm in accordance with some embodiments.
Figure 3A:
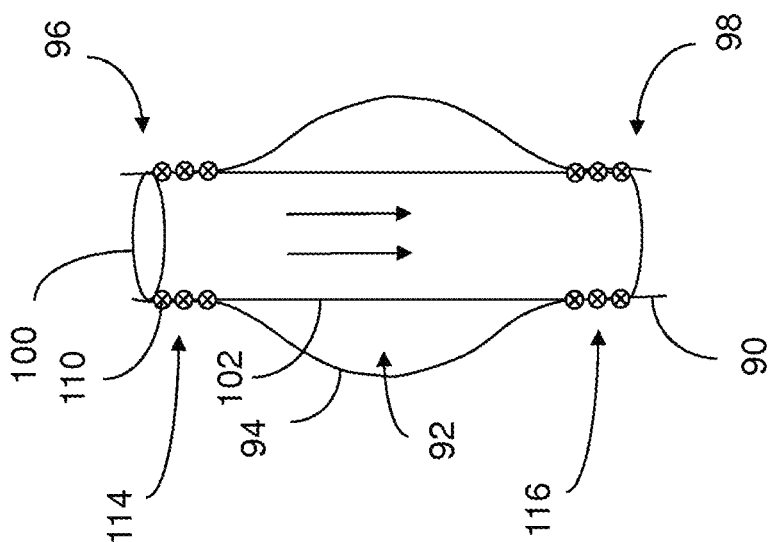

FIGS. 3A and 3B depict an illustrative embodiment where a device for treating a vessel 90 having developed an aneurysm 94 is deployed in the vessel which is located, for example, at a thoracic or abdominal aortic location. The device includes a conduit 100 having coupling members 110 (e.g., hooks, barbs, adhesives, attachment tools, sutures, staples, etc.) disposed at end portions 114, 116 of the conduit. The coupling members function to couple portions of the conduit and the vessel together at suitable regions 96, 98 of the vessel. The aneurysm 94 is depicted as a region having an abnormal bulge that forms a space 92 between the inner wall of the enlarged region of the vessel and the exterior surface 102 of the conduit. As shown, the exterior surface 102 of the conduit is spaced inward from an interior surface of the vessel where the aneurysm is present.

In some embodiments, the conduit includes a barrier material (e.g., membrane) attached to the conduit for reducing leakage of fluid between the interior and exterior of the conduit. The barrier material may form a lumen within the conduit through which fluid may substantially flow. In some embodiments, a membrane is attached to and covers the conduit for reducing leakage of fluid traveling through the internal lumen of the conduit. For example, a lumen may be formed by the conduit from the presence of the membrane. The membrane may include any suitable biocompatible material (e.g., polymer, fabric, etc.), such as but not limited to, polytetrafluoroethylene (PTFE, GORE-TEX®), silicone elastomer (e.g., SILASTIC®), polyethylene terephthalate (e.g., DACRON®), polyurethane, polyester, or the like. In some embodiments, the membrane may provide a seal between the conduit and the vessel wall, and may be used in place of and/or in cooperation with a sealing material, which is further described below.

In some embodiments, a membrane is disposed within the lumen of the conduit. For example, the membrane may be attached to support members of the conduit so as to line the interior surface of the conduit. In some embodiments, a membrane is stretched over or mounted on an exterior surface of the conduit. For instance, the membrane may cover the support members (e.g., longitudinal/transverse beams, struts) of the conduit. Alternatively, a membrane may be integrated along with support members of the conduit, for example, the membrane may be structured to have channels through which support members of the conduit are disposed.

In some embodiments, the membrane includes multiple layers, for example, an outer layer and an inner layer.

An outer layer of the membrane may be suited to promote a stable interface and/or seal with the vessel wall, and/or encourage fibroblast ingrowth, scar/collagen formation, or the like. For example, the outer layer may include a certain composition, may be drug-eluting, and/or may exhibit a porosity that assist in providing such characteristics. In some embodiments, the outer layer of the membrane includes an appropriate fabric or polymer that stimulates or otherwise promotes healing/stabilization of the vessel (e.g., aorta). An outer layer of the membrane may include any appropriate material, such as PTFE (e.g., GORE-TEX®, silicone elastomer (e.g., SILASTIC®), polyethylene terephthalate (e.g., DACRON®), polyurethane, polyester, etc. Such as a layer may or may not be in direct contact with the vessel wall.

An inner layer of the membrane may include a generally smooth luminal surface that may be in contact with the blood stream. In some cases, the inner layer may prevent or obstruct fibroblast or intimal growth into the lumen of the vessel. By substantially discouraging migration of tissue/cells into the lumen of the vessel, undesirable narrowing of the blood vessel (i.e., stenosis) may be averted.

In some embodiments, end portions 114, 116 of the conduit are close enough together such that the device is essentially provided as a ring. For example, the ratio of the diameter of the conduit to the distance between ends of the conduit is greater than 1, greater than 2, greater than 3, greater than 4, greater than 5 (e.g., between about 1 and about 10, between about 1 and about 5), etc. In such embodiments, similar structural and functional considerations exist, and the device may be employed in regions where anatomic space is significantly limited. Accordingly, a device structured as a shortened conduit (e.g., ring) may be used/deployed in a highly localized treatment of a small region of abnormal and/or dilated vessel (e.g. aortic root, aortic sinus). In some embodiments, a shortened conduit may be placed in the aortic root for treating aortic root dilation.

Because the tissue of an abnormally enlarged region of an abdominal or thoracic aortic aneurysm may be quite weak and unable to support a physical attachment or anchoring arrangement, coupling members of some embodiments of devices described herein may be located at end portions of the conduit, similar to that shown in FIGS. 3A and 3B. Accordingly, healthier regions of the vessel that have sufficient tissue integrity to support a physical attachment or anchoring arrangement may be coupled to the conduit. As such, devices similar to the embodiments illustrated in FIGS. 3A and 3B may be suitable for implantation and deployment in regions where an abdominal or thoracic aortic aneurysm has occurred.

As shown in FIGS. 3A and 3B, upon suitable deployment of the device, fluid may pass through the internal lumen of the conduit as illustrated by the solid arrows. As the fluid travels through the conduit, the fluid does not contact the inner wall of the enlarged region of the vessel where the aneurysm is present. By providing an alternative path through which fluid may flow, the fluid that flows through the lumen of the conduit contributes significantly less, or not at all, to pressure (e.g., hydrostatic, hydrodynamic) experienced by the enlarged region of the vessel where tissue is substantially weakened, absent the conduit. In some embodiments, the conduit may have features that exhibit elastic characteristics (e.g., membrane, support members) that may function to absorb cyclical pressure/energy transfer that may be present in the vessel (e.g., aorta) due to pumping forces that arise during systole and diastole. By absorbing pressure/energy transfer arising from systole and diastole, the implanted device provides further relief for the weakened tissue at the region of abnormal enlargement.

FIG. 3B depicts relative constriction of the conduit 100 resulting in the exertion of an inward radial force, shown by the dashed arrows, at the regions 96, 98 of the vessel wall where the coupling members 110 located at end portions 114, 116 of the conduit are attached. In this embodiment, the diameter of the conduit constricts radially and coupling members 110 disposed at end portions 114, 116 are attached to both the conduit and the vessel wall so as to create a pulling force on the inner surface of the vessel wall at regions 96, 98. Though, in some embodiments, upon coupling to the vessel wall, the conduit 100 expands or maintains the diameter of the vessel without exertion of an inward radial force on the vessel wall. Accordingly, a conduit may be coupled to a diseased/weakened vessel wall, or region adjacent to the diseased/weakened vessel wall, with negligible constriction, if any at all, of the vessel wall.

As illustrated in FIGS. 3A and 3B, no coupled attachment exists between the vessel and the conduit at a midpoint region of the conduit between end portions 114, 116 immediately adjacent to where the vessel has experienced excessive dilation. Rather, coupling members 110 are attached to tissue at opposite ends 114, 116 of the conduit on either side of the aneurysm 94 where the tissue is comparatively healthier than the tissue of the aneurysm. In some cases, the enlarged region of the vessel has experienced so much dilation or structural degradation that the conduit is unable to expand far enough along its diameter for a coupling member to suitably engage the vessel wall. In some cases, however, the conduit is able to expand far enough for a coupling member to engage the vessel wall, though, the tissue of the excessively dilated region of the vessel is not strong enough for a suitable physical attachment between a coupling member and the tissue to occur. In other words, no suitable anchor can be established by the coupling member between the conduit and the dilated region of the vessel because the tissue is so weak that it is unable to be suitably pulled inward. In some cases, the tissue integrity becomes relatively gelatinous in consistency such that it is unable to support an attachment or hold its shape upon application of a force. In some instances, the tissue lacks structural resistance such that the coupling member would simply pass through the weakened tissue upon attempted engagement.

The tissue of the abnormally enlarged region of an aneurysm that has developed in other vessels (e.g., ascending aorta), in some cases, may be generally healthier than the tissue of the abnormally enlarged region of an abdominal or thoracic aneurysm. In some instances, regions of an ascending aortic aneurysm may dilate to diameters that are approximately 30-50%, or over 100% greater than the diameter of a corresponding region of a normal ascending aorta that is not subject to an aneurysm. On the other hand, the percentage increase in diameter of affected regions of a vessel in an abdominal or descending thoracic aortic aneurysm may be greater than is generally seen in an ascending aortic aneurysm. The tissues of an ascending aortic aneurysm are also, generally speaking, less atherosclerotic and, therefore, potentially more robust than tissues of an abdominal or descending thoracic aortic aneurysm. Tissues of an ascending aortic aneurysm may also, in some cases, be more tubular in geometry, rather than markedly saccular or fusiform. Accordingly, the tissue of an enlarged region of an aneurysm having developed in the ascending aorta may be able to adequately support a physical attachment coupling. As such, since dilated regions of the ascending aorta may be strong enough to be physically coupled to and manipulated with a conduit, devices for mitigating an aneurysm developed at an ascending aorta may include coupling members located at frequent intervals along the conduit between opposing ends of the conduit (e.g., at a midpoint region), similar to that shown in FIGS. 4A and 4B.

Figure 4B:
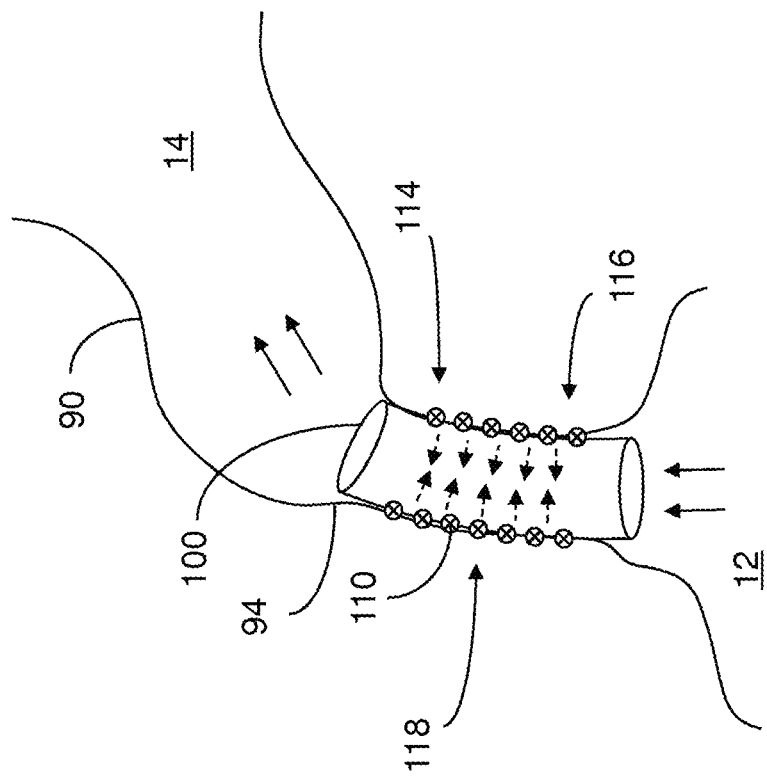
FIGS. 4A-4B depict schematics of other treatment methods and devices for an aneurysm in accordance with some embodiments.
Figure 4A:
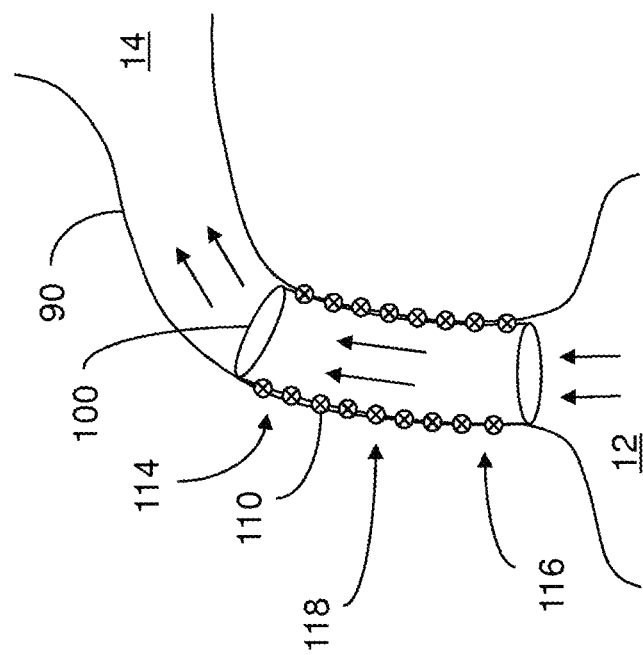

FIGS. 4A and 4B depict an embodiment of a device for treating a vessel 90 deployed at an ascending aortic region that is subject to the occurrence of an aneurysm, for example, an aneurysm has occurred or weakening of the vessel wall is detected such that the development of an aneurysm is imminent. The device includes a conduit 100 where coupling members 110 (e.g., hooks, barbs, adhesives, attachment tools, sutures, staples, etc.) are disposed along the length of the conduit. The coupling members 110 may be disposed not only at opposite ends of the conduit at end portions 114, 116 but also between opposite ends of the conduit at a midpoint region 118 of the conduit. The midpoint region of the conduit may be a region where the distance to either end (e.g., end portions 114, 116) is about the same. In such embodiments, the tissue, albeit weakened in comparison to normal healthy tissue, is strong enough having a sufficient amount of structural strength such that a coupling member may form a suitable physical attachment between the conduit and the vessel. For some situations, and as discussed previously, the tissue of a vessel wall having developed an aneurysm in the ascending aorta may be comparatively stronger than the tissue of a vessel wall where an aneurysm has developed in other areas (e.g., abdominal or thoracic aortic regions).

In FIGS. 4A and 4B, blood flow from the heart 12 through the ascending aorta and to the aortic arch 14 is depicted by the solid arrows. As shown in FIG. 4B, the vessel 90 has developed an aneurysm 94, yet because the conduit is attached to the wall of the ascending aorta and pulls the vessel inward, undesirable dilation of the ascending aorta to a greater degree is substantially reduced at the region(s) of attachment. In addition, when placed in a fully deployed configuration, the diameter of the conduit is constricted such that coupling members 110 of the conduit provide an inward radial pulling force, illustrated by the dashed arrows, to the region of the vessel wall where coupling members are attached. As a result, the vessel wall is pulled radially inward so as to conform to the shape of the deployed conduit. Accordingly, the diameter of the vessel wall at regions where the vessel is coupled to the conduit is smaller than what the diameter of the vessel wall would be without such coupling of the vessel and the conduit.

FIG. 5 depicts a schematic of another illustrative embodiment of an implanted device including a conduit 100 and coupling members 110 that is deployed in a vessel 90 that has developed an aneurysm 94. Healthy regions of vessel (i.e., regions of the vessel where an aneurysm is not present) that are located on the periphery of the aneurysm have a natural vessel diameter $d_v$ (or vessel width). Yet, regions of the vessel where the aneurysm has developed may experience abnormal dilation such that an enlarged portion of the vessel has an aneurysm diameter $d_a$ (aneurysm width), which is substantially larger than the natural vessel diameter $d_v$. Dashed lines, shown in FIG. 5, illustrate the region of vessel enlargement that would result from the occurrence of the aneurysm absent deployment of the device for treating the aneurysm.

When the device is appropriately deployed, the coupling members of the conduit attach to the vessel wall at a region where abnormal enlargement has occurred or is thought to occur. As shown in FIG. 5, coupling members are disposed along the majority of the exterior surface of the conduit, such as at opposing ends of the conduit as well as along a midpoint region of the conduit. Upon attachment of the conduit and the vessel, the coupling members form a connection between the vessel and the conduit such that the shape of the conduit affects the shape of the vessel at the points where the coupling members are attached. As depicted in FIG. 5, the conduit is constricted so as to pull the vessel radially inward at the region(s) where coupling members are attached. Accordingly, the implanted device brings the region of the vessel that is prone to abnormal enlargement to have a constricted diameter $d_c$ (or constricted width), in conformance with the diameter of the conduit. In some embodiments, the constricted diameter $d_c$ of the conduit is the diameter of the conduit when it achieves an equilibrium state.

The constricted diameter $d_c$ of the vessel when the implanted device is deployed within the vessel is shown in FIG. 5 to be less than the aneurysm diameter $d_a$ of the vessel when the device is not deployed within the vessel. That is, for some embodiments, when the device is suitably deployed, the constricted diameter $d_c$ of the vessel at a region subject to the development or further risk of an aneurysm is less than an aneurysm diameter $d_a$ of the vessel when the device is not deployed in the vessel. While being distinct non-limiting embodiments, the schematic of FIG. 5 is similar to that shown in FIG. 4B in that coupling members are located along the length of the exterior surface of the conduit including at a midpoint region so that the coupling members are able to couple with weakened tissue that is subject to an aneurysm and, in some cases, pull the tissue radially inward.

The conduit may include any suitable structure. For example, the conduit may include a number of support members (e.g., beams, struts) oriented in a generally longitudinal and/or transverse direction with respect to the conduit. Support members may be arranged in accordance with a suitable structure appropriate for deployment within a vessel. In some embodiments, the conduit is a stent-like device having elastic support members that allow the conduit to be subject to alterations in shape during deployment. As described further below, for some embodiments, when deployed, the conduit includes a structure having ringed ends with longitudinal support members and elastic members disposed between and connecting the ringed ends. The longitudinal support members may be positioned in cooperation with one another so as to result in a conduit having an adjustable shape. The elastic members may function to bring the conduit to conform to an equilibrium shape.

FIGS. 6A-6D depict an illustrative embodiment involving a process where a device having a conduit 100 and coupling members 110 is suitably implanted in a vessel 90 where an aneurysm 94 is present. A healthy portion of the vessel where the aneurysm has not occurred has a natural vessel diameter $d_v$. However, an abnormally enlarged region of the vessel where the aneurysm has occurred has an aneurysm diameter $d_a$, which is larger than the natural vessel diameter $d_v$. In an embodiment, the device is deployed into the vessel through a suitable catheter assembly which may include an appropriate guide wire 120 and an expansion member 122 (e.g., balloon). In some embodiments, a suitable device may be implanted in a vessel where an aneurysm is not yet present or is considered to be at risk for development of an aneurysm.

Figure 6A:
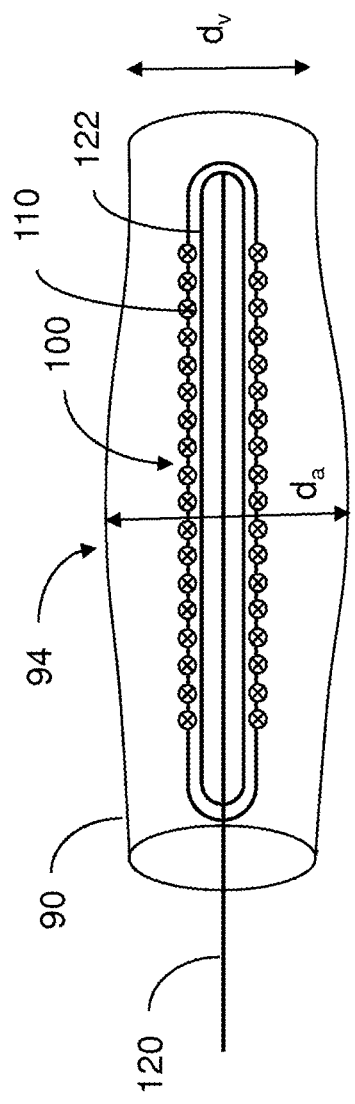

In FIG. 6A, the device is incorporated in a catheter assembly where the assembly is navigated through various passageways in the body and ultimately to the region of deployment. In some embodiments, a sheath (not shown in the figures) is provided in the catheter assembly to surround the device to be implanted. The presence of a sheath may be beneficial to provide a suitable degree of protection for the device enclosed within the sheath during navigation of the device to the region of deployment. The sheath may also serve to constrain the device from expanding to its equilibrium conformation until it reaches an appropriate location. The sheath may be removed at an appropriate time such as when the device is ready to be placed in a fully deployed configuration. For example, the sheath may be removed when the assembly is suitably positioned immediately prior to expansion of the conduit.

Figure 6B:
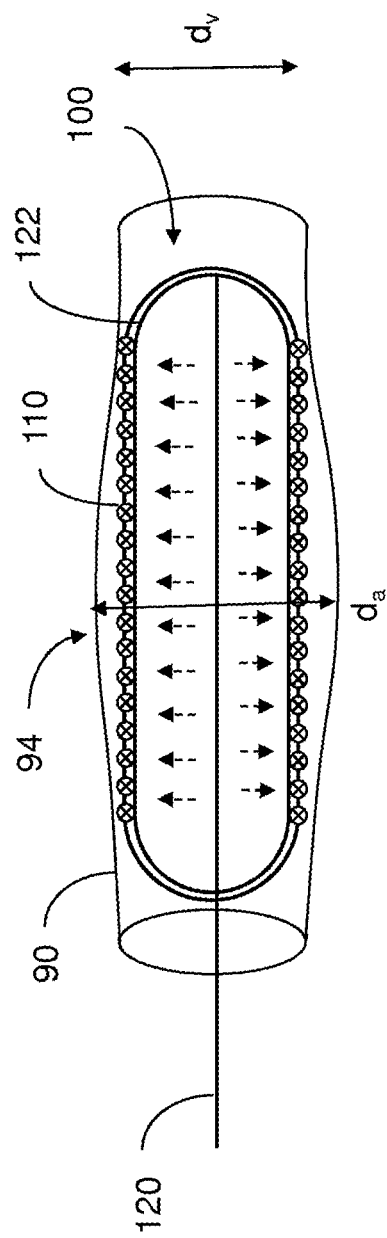

As depicted in FIG. 6B, the expansion member 122 may optionally apply an outward directed pressure to the conduit 100 for expanding the conduit into the vessel wall such that coupling members are able to engage with the vessel wall. The expansion member 122 continues to expand, as shown in FIG. 6C, and applies outward pressure to both the conduit 100 and the vessel 90. In some cases, the expansion member does not expand the conduit but simply allows the device to be inserted into the vessel to match the size of the untreated vessel. Upon full deployment (e.g., enlargement) of the expansion member, the conduit presses up against the vessel such that both the conduit and the vessel exhibit an expanded diameter $d_e$ which is greater than both the natural vessel diameter $d_v$ and the original aneurysm diameter $d_a$. In some embodiments, however, the expanded diameter $d_e$ is less than the original aneurysm diameter $d_a$ or, in some cases, the expanded diameter $d_e$ is even less than the natural vessel diameter $d_v$.

In some cases, expanding the lumen of the conduit may assist in forming a coupled arrangement between the coupling members 110 and the wall of the vessel 90. For example, expansion of the exterior surface of the conduit into the vessel wall may cause coupling members to be suitably oriented in a manner that provides for engagement of the conduit and the vessel to form an attachment between the conduit and the vessel. In some cases, coupling members disposed on the exterior surface of the conduit are configured to couple with the vessel wall automatically upon expansion and pressing of the conduit against the vessel. For example, expansion of the conduit may cause a sharp end of a coupling member (e.g., hook, barb, pin) to point toward the vessel so that the coupling member may be easily inserted into the vessel wall. In other cases, coupling members may be manually manipulated (e.g., by a twisting or pulling motion, with a suitable tool/instrument, etc.) to form a coupled arrangement between the conduit and the vessel wall. For example, during deployment, a user may manipulate the catheter assembly, such as through an appropriate twisting or pulling motion in a manner that enables the coupling members to suitably engage the vessel wall. In some embodiments, a separate instrument is used to appropriately set the coupling members. In some embodiments, coupling members are not originally included on the conduit, but rather, are provided via a separate instrument for coupling the conduit and the vessel together.

In some cases, an expansion member is not required; that is, upon removal of the optional sheath, the conduit self-expands and becomes suitably attached to the vessel wall (e.g., via coupling members). As noted above, the conduit is not required to expand, but may be positioned within the vessel in a manner that does not alter the size of the lumen.

In some embodiments, the device is mounted within an appropriately sized docking structure or stent-like device predisposed within the vessel. As such, a docking structure or stent-like device (not shown in the figures) may act as a coupling member in providing a manner through which the conduit and the vessel may be physically attached. In an embodiment, the docking structure is expanded into position within the vessel prior to deployment of the device having the conduit, for example, via inflation of a separate expansion member (e.g., balloon). The docking structure may have suitable receiving features through which the conduit may form a connection with the docking structure. Additional coupling members of the conduit may optionally be used in attaching the conduit to the docking structure. That is, the conduit may have coupling members for forming an attachment with a docking structure and the docking structure may further serve as a coupling member for attaching the docked conduit to the vessel. In another embodiment, the docking structure is incorporated into the deployment apparatus (e.g., catheter assembly) and deployed jointly with the device for treating the vessel. In various embodiments where a docking structure is incorporated, the conduit and the docking structure may be attachable and via any suitable method.

The expansion member 122 may be removed from the region of implantation, for example, when coupling members are suitably in place for coupling to occur between the conduit and the vessel. In some embodiments, upon removal of the expansion member, the conduit constricts to a target shape for the final stage of deployment. In some embodiments, the expansion member is a balloon that is expanded so that the conduit and coupling members suitably engage with the vessel wall and is then deflated so that the balloon can be subsequently removed.

In some embodiments, as discussed above, coupling members include appropriately shaped hooks or barbs that are inserted into the vessel wall when the conduit is pressed up against the wall. When the conduit is constricted (e.g., when the balloon is deflated), the hooks may naturally re-orient (e.g., twist, rotate) so as to automatically form a coupled arrangement between the conduit and the vessel wall upon deployment. In some embodiments, the balloon is deflated in a controlled manner so as to produce rotation of the hooks to an equilibrium configuration so that the hooks are subsequently set into the vessel wall. In some cases, as the device relaxes into equilibrium, the vessel wall is pulled or drawn inward.

As depicted in FIG. 6D, the guide wire 120 and an expansion member 122 are removed from the vessel 90 and the conduit assumes a deployed configuration where the final constricted diameter $d_c$ of the vessel is optionally smaller than the natural vessel diameter $d_v$. In some embodiments, the final constricted diameter $d_c$ is not smaller than the natural vessel diameter $d_v$ (e.g., remains larger than the natural vessel diameter $d_v$ or is similar in size to the natural vessel diameter $d_v$). When the final constricted diameter $d_c$ of the vessel is smaller than the natural vessel diameter $d_v$ or the original aneurysm diameter $d_a$, the portion of the vessel which is coupled to the conduit is pulled radially inward and held by the conduit to maintain the constricted diameter $d_c$. Accordingly, the conduit physically restrains radially outward movement of the vessel, reducing the risk of vessel rupture or dissection due to further dilation of the vessel.

As noted above, the equilibrium diameter of the conduit may be approximately the same as the initial diameter of the vessel while in an untreated state (e.g., slightly enlarged). For instance, the untreated vessel may have an initial diameter of 4 cm and it may or may not be feasible or appropriate to pull the vessel walls inward to a much smaller diameter, for example, 3.5 cm. In such a situation, the device, possibly through a combination of physical restraint and scar formation, may substantially prevent the vessel from radially enlarging while not pulling the vessel walls to a lumen size that is significantly smaller than the lumen size of the untreated vessel. For example, the device may be inserted into a vessel where the equilibrium size of the conduit is essentially the same as that of the untreated vessel. Once fully deployed, the device may effectively maintain the vessel at the original size (i.e., preventing further/ongoing dilation) without pulling the vessel wall inward so as to decrease the initial size of the untreated vessel lumen. Accordingly, in some embodiments, the device may be deployed in a manner that does not shrink the lumen of the vessel, but may couple with the vessel to maintain its lumen size (e.g., diameter).

The natural vessel diameter $d_v$ of the vessel (e.g., ascending aorta, aortic arch, descending thoracic aorta, abdominal aorta, intestine, urethra) may fall within a suitable range. In some embodiments, the natural vessel diameter $d_v$ is between about 2 cm and about 5 cm, or between about 3 cm and about 4 cm.

The expanded diameter $d_e$ to which the vessel expands during deployment of the device may also fall within a suitable range. In some embodiments, the relationship between the expanded diameter $d_e$ and the natural vessel diameter $d_v$ relates to the starting diameter of the vessel, which may not necessarily be uniform along its length, and also the size and characteristics of an appropriately chosen conduit. In some embodiments, the expanded diameter $d_e$ of the vessel is between about 3 cm and about 7 cm, between about 3.5 cm and about 6 cm, or between about 4 cm and about 5 cm. In some embodiments, the expanded diameter $d_e$ of the vessel is between about 20% and about 100% greater than the natural vessel diameter $d_v$, between about 30% and about 70% greater than the natural vessel diameter $d_v$, or between about 40% and about 50% greater than the natural vessel diameter $d_v$.

The final constricted diameter $d_c$ to which the vessel is decreased along with the constricted conduit may fall within a suitable range. In some embodiments, the diameter $d_c$ of the vessel (e.g., ascending aorta, aortic arch, descending thoracic aorta, abdominal aorta, intestine, urethra) is constricted to a distance of between about 2 cm and about 5 cm, between about 2.5 cm and about 4 cm, or between about 3 cm and about 3.5 cm. In some embodiments, the constricted diameter $d_c$ of the vessel is between 0% and about 50% smaller than the natural vessel diameter $d_v$ (e.g., the constricted diameter $d_c$ of the vessel may be approximately the same as the natural vessel diameter $d_v$), between about 5% and about 40% smaller than the natural vessel diameter $d_v$, between about 10% and about 30% smaller than the natural vessel diameter $d_v$, or between about 15% and about 20% smaller than the natural vessel diameter $d_v$.

In an example, an appropriate catheter assembly is used to insert the conduit with coupling members into an ascending aortic region having a natural vessel diameter $d_v$ of about 4 cm. Upon expansion of the vessel (e.g., through pressure applied via a balloon), the diameter of the vessel at the region of coupling increases to an expanded diameter $d_e$ of between about 4 cm and about 5 cm (e.g., about 4.5 cm, or about 5 cm). Once the conduit is suitably coupled to the vessel wall, the conduit constricts bringing the vessel at the coupled region to a final constricted diameter $d_c$ of between about 3 cm and about 3.5 cm (e.g., about 3.5 cm, or about 3 cm).

In some embodiments, the device for treating vessels may incorporate within support members of the conduit a shape memory alloy material, which is an alloy of metals (e.g., combinations of copper, zinc, nickel, aluminium, titanium, or other metals) that, subject to certain conditions, may assume a pre-programmed conformation despite manipulation and deformation. Under certain conditions, these materials exhibit a phase change that affects the mechanical characteristics of the material. For example, nitinol (nickel-titanium alloy) may be incorporated in suitable devices described herein. Austenite and martensite, the two phases under which nitinol exists, have unique molecular structures. When subject to changes in temperature or applied stress, nitinol may exhibit fluid transitions between austenite and martensite phases. Such materials that exhibit phase change behaviour may, in turn, affect the overall elastic and compressibility properties of the device. For instance, while martensite has malleable characteristics, a sufficient change in temperature or applied pressure will cause a nitinol material to transition to an austenitic state, upon which the nitinol material resumes a prior pre-programmed conformation. While materials such as alloys described above have intrinsic characteristics, conformational changes possible for the device in question need not be constrained by the linear limitations of the materials. In other words, nitinol is known to exhibit elasticity, being able to stretch to approximately 110% of its resting length without permanent distortion.

While any individual element fabricated from nitinol would be limited by this physical characteristic, the device may be designed in such a way that secondary structure plays a large role in the conformational changes that the device is capable of undergoing. For example, intricate cutting patterns in stent-making can be significant in determining the behaviour of the stent when expanded. Similarly, elements which, in addition to their linear elasticity, may also undergo changes in conformation or shape via bending and unbending, curling and uncurling, allow for a greater flexibility in device design and conformational possibilities of the device as a whole. Portions of the device, or the entire device itself, may be fabricated from a metal alloy tube such as a nitinol tube, involving casting, laser-cutting, welding, or another suitable fabrication method.

The device may be suitable for radiographic imaging. In some embodiments, the device includes one or more materials that are appropriately placed and can be well viewed radiographically. Accordingly, the device may include radioopaque markers, for example, made of gold, platinum or other radioopaque metal/material. Radiographic materials may allow for the device to be positioned under fluoroscopic guidance, and may provide for X-ray evaluation(s).

FIGS. 7A and 7B depict a number of illustrative embodiments of various coupling members 110a, 110b, 110c, 110d, 110e, 110f, 110g which serve as suitable coupling members to attach the conduit 100 and the vessel wall 90 together. Each of the coupling members 110a, 110b, 110c, 110d, 110e, 110f, 110g provide an anchoring function between an exterior surface of the conduit and an interior wall surface of the vessel. Any suitable coupling member(s) may be used to couple the conduit and the vessel to one another as arrangements involving components other than coupling members 110a, 110b, 110c, 110d, 110e, 110f, 110g may also be employed. Furthermore, although the coupling members are depicted in two dimensions and shown to engage the vessel wall via movement along the longitudinal axis of the conduit (i.e., parallel to the general direction of flow through the vessel), rotation of the coupling members may also involve movement of coupling members in a direction perpendicular to the longitudinal axis of the conduit, or a combination thereof. That is, the device may be twisted within the vessel lumen so as to set the coupling members in the vessel wall at an orientation that may be oblique and/or parallel to the longitudinal axis of the vessel.

Coupling member 110a is depicted as a pin arrangement having a relatively sharp end 112a and an opposite end 113a attached to the conduit (e.g., attached to a support member of the conduit) and optionally rotatable relative to the conduit. The cross section of the pin (or any alternative coupling members in accordance with embodiments described herein) may have any appropriate shape (e.g. circular, rectangular or other). Suitable structure(s) of a coupling member may be relatively thin (e.g., pin-like), or may have fairly broad (e.g., relatively thick) dimensions. The relatively sharp end may be inserted into the vessel wall and, upon suitable rotation or twisting of the conduit and/or the coupling member relative to the vessel, the pin arrangement may provide for attachment between the conduit and the vessel. As shown in FIG. 7A, the coupling member 110a is manipulated in a manner such that the sharp end of the coupling member engages with the vessel wall. Subsequently, as shown in FIG. 7B, the coupling member is rotated relative to the vessel such that the exterior surface of the conduit and an inner surface of the vessel are brought together, forming a coupled arrangement between the conduit and the vessel.

Coupling member 110b includes a sharp end 112b having a suitable curvature (e.g., hook, barb) and an opposite end 113b attached to the conduit. The sharp end serves to couple the conduit and vessel wall together upon suitable rotation of the conduit relative to the vessel. For instance, the coupling member 110b may be rotatably inserted into the vessel wall initially via the sharp end. Upon further rotation, the coupling member 110b appropriately anchors the conduit and the vessel wall together.

Coupling member 110c has a pair of sharp ends 112c with suitable curvature and opposite ends 113c each similar to the structure of the single coupling member 110b. When the pair of curved members of the coupling member 110c are inserted into the vessel wall and rotated in concert, the conduit and vessel wall are also brought together into a suitably coupled arrangement.

Coupling member 110d includes a dual element coupling arrangement where a pair of insertion ends 112d of the coupling member are inserted into the vessel wall to establish an initial connection between the conduit and the vessel, as shown in FIG. 7A. The coupling member 110d also includes a pair of attachment ends 113d that may be rotated and coupled together to form a unitary component for providing a more secure attachment between the conduit and the vessel. The coupling member 110d, attached to the conduit, may be inserted into the vessel wall so as to be appropriately situated between the vessel wall and the conduit, as illustrated in FIG. 7A. The insertion ends 112d may be manipulated (e.g., bent, pivoted) to take on an outward facing shape, or inward facing (not shown), with respect to one another so as to form an anchor with the vessel. Similarly, the attachment ends 113d may also be alternatively arranged (e.g., angled toward rather than away from one another) to form a suitably coupled arrangement. Accordingly, as shown in FIG. 7B, the attachment ends 113d provide for the dual elements of the coupling member 110d to function as a single unitary component (which in some embodiments may be via attachment to one another) and the insertion ends 112d provide for secure anchoring of the conduit and the vessel wall together.

Coupling member 110e is similar to coupling member 110d in structure and function, yet the pair of insertion ends 112e of the member extend completely through the vessel wall to the exterior side of the vessel. The attachment ends 113e of the coupling member 110e are similar to the attachment ends 113d and may be appropriately coupled together similar to that described above for coupling member 110d where a single unitary component is formed. Upon insertion of the coupling member 110e through the vessel wall, the insertion ends 112e may be manipulated to form an anchor with the vessel. The attachment ends 113e may also be manipulated to be coupled together so as to further secure the conduit and the vessel wall to one another.

Coupling member 110f is similar to coupling member 110d in structure and function when placed in a coupled arrangement, yet the attachment end 113f connects the insertion ends 112f such that the member is already formed as a single unitary component. Upon insertion of the coupling member 110f through the vessel wall, the insertion ends 112f may be manipulated to form an anchor with the vessel (e.g., inward facing, outward facing, or otherwise) so as to couple the conduit and the vessel together.

Coupling member 110g includes a pin-type arrangement having a relatively sharp collapsed end 112g and an opposite end 113g attached to the conduit (e.g., attached to a support member of the conduit). As shown in FIG. 7A, the relatively sharp collapsed end may be inserted into the vessel wall. Upon suitable manipulation (e.g., rotation, twisting, actuation) of the conduit and/or the coupling member, as depicted in FIG. 7B, the relatively sharp collapsed end 112g may open into a disk-like configuration so as to form a coupled arrangement between the conduit and the vessel. In some embodiments, the relatively sharp collapsed end 112g opens in a manner similar to that of an umbrella into the broader conformation to form the coupled arrangement.

FIGS. 7C and 7D show a coupling member 110h for attachment at the entrance or within the sinuses of valsalva 21. The coupling member 110h includes a sharp end 112h with a suitable curvature (e.g., hook, barb) and an opposite end 113h attached to the conduit. The sharp end serves to couple the conduit and vessel wall together upon suitable movement of the conduit relative to the vessel. For instance, the coupling member 110h may be inserted into the vessel wall initially via the sharp end by pulling the device into the tissue wall of the sinus of valsalva 21, located immediately adjacent to the aortic valve. Upon further actuation, the coupling member 110h appropriately anchors the conduit and the vessel wall together so as to restrain the device from undesirable movement and to inhibit slippage of the device downstream. In some embodiments, a coupling member is seated within the sinuses of valsalva so that at least a majority of the coupling member is located within the region encompassed by the cusps.

The coupling arrangement may include any other suitable coupling member. In some embodiments, a coupling member includes an appropriate medical stitch, suture or staple for attaching and securing the conduit to the vessel wall. In some cases, a separate coupling member (not shown in the figures) that is not pre-attached to the conduit may be used to couple the conduit and the vessel wall together. For example, a fixation device, such as an endovascular stapler, suturing instrument, or other suitable device may be used to form an attached arrangement between the conduit and the vessel wall. Accordingly, in some embodiments, for a device that does not include its own coupling members and/or could use one or more supplemental forms of attachment to the vessel wall, a suitable fixation device may be employed to secure the conduit to the vessel wall.

In some embodiments, expansion of the device within the vessel during deployment serves to manipulate a coupling member disposed on the conduit (e.g., attached to a support member) to an open configuration where the coupling member is oriented in a manner that invites suitable engagement with the vessel wall. The conduit is expanded to a sufficient degree such that the coupling member in the open configuration engages with the vessel wall (e.g., inserted into the vessel wall). The conduit then relaxes from the expanded state to an equilibrium conformation that, in turn, allows the coupling member to recoil into a closed configuration, along with the device as a whole, providing a secure attachment for the conduit to constrict and pull the vessel radially inward and/or into close apposition with the vessel wall.

As discussed above, upon suitable deployment of the implantable device, fluid flow through the vessel may, in large part, be directed through the internal lumen of the conduit so as to reduce pressure build up at the region where tissue is substantially weakened. By reducing pressure at a region of weakened tissue, the risk for further vessel dilation to excessively occur is mitigated. As discussed previously, in some embodiments, when the implantable device is fully deployed, leakage of fluid between an interior region and an exterior region of the conduit is obstructed. For example, upon coupling of the conduit with the vessel wall, a barrier to fluid flow between the coupled portion of the conduit and the vessel wall may be formed. Rather than contacting the vessel wall during flow through the vessel, fluid is diverted through the internal lumen provided by the conduit. In some cases, such a barrier may provide a seal between the coupled portion of the conduit and the vessel wall.

Figure 8:
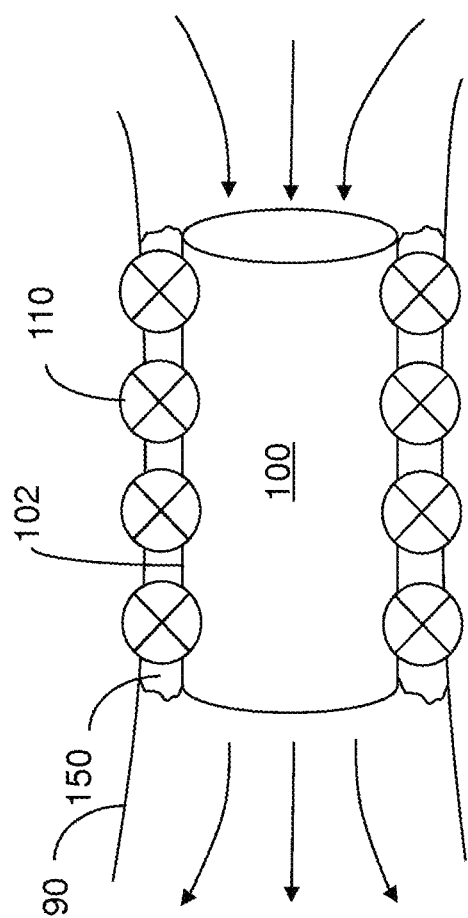
FIG. 8 depicts a device deployed in a vessel in accordance with some embodiments.

FIG. 8 illustrates an embodiment of a device in a deployed configuration for treating a vessel 90 where an aneurysm has developed or is considered likely to develop. Coupling members 110 serve to attach the conduit 100 and the wall of the vessel together. In an embodiment, a sealing material 150 is provided between the exterior surface 102 of the conduit and the vessel wall so as to obstruct fluid from flowing in the region between the exterior surface of the conduit and the vessel wall. Such an obstruction of fluid may be advantageous as it may result in a substantial reduction of pressure applied to the weakened tissue of the aneurysm due to diversion of the fluid away from the weakened tissue.

Any suitable sealing material may be used to reduce the likelihood of leakage or fluid flow from the internal lumen to outside of the conduit. In some embodiments, such a sealing material includes a polymer, hydrogel, a suitable inorganic or organic filler material, or any other appropriate material. The sealing material may be a generally inert sealant.

Alternatively, the sealing material may include a composition that encourages ingrowth of cells (e.g., fibroblasts) and formation of connective tissue and/or scar, allowing for the device to be suitably incorporated biologically and structurally into the vessel wall. In some instances, the sealing material may be moldable, at least initially, so as to suitably conform to the space between the conduit and the vessel wall. Once the sealing material is adequately molded between the conduit and the vessel wall, the sealing material may be appropriately cured.

In some embodiments, the sealing material may be used in cooperation with a membrane, such as that described above. Alternatively, the membrane itself, or other barrier, may serve as a sealing material.

The sealing material may be delivered to or with the conduit in an appropriate manner. For example, the sealing material may be provided as part of the conduit, or may be packaged and delivered to the vessel along with the conduit. In some embodiments, the sealing material is provided in a separately deployable tube that follows the device, or is followed by the device, during deployment and which may be positioned adjacent the vessel wall so as to release the sealing material.

Figures 9A, 9B:
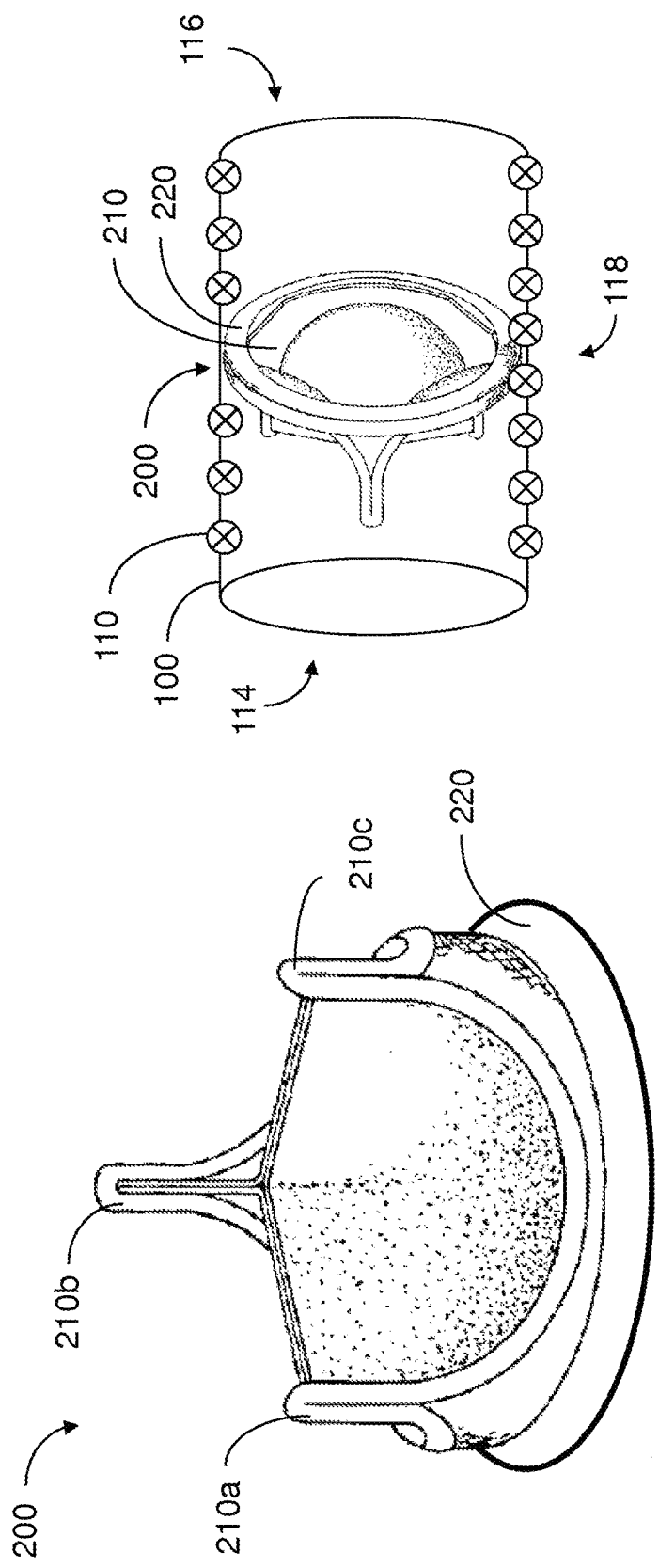
FIG. 9A depicts a prior art valve for use with a device in accordance with some embodiments.
FIG. 9B illustrates a device incorporating the valve of FIG. 9A in accordance with some embodiments.

Suitable embodiments of the device for treating vessels may incorporate various components and/or features, such as valves, stents, coupling members, support members and bendable conduits. FIG. 9A depicts a prosthetic valve 200 having as many as three valve leaflets 210a, 210b and 210c attached to a valve frame 220 for implantation at a suitable region of the heart. FIG. 9B depicts the valve 200 incorporated within the lumen of a conduit 100 where the conduit includes appropriately positioned coupling members 110 along the length of the conduit. The valve is located at a midpoint region 118 of the conduit disposed between opposing ends 114, 116 of the conduit. The valve may be secured within the conduit in any suitable manner. In some embodiments, the valve is included with a catheter assembly (e.g., transcatheter valve assembly) and may be suitably deployed in a vessel along with the conduit and coupling members.

Figure 9C:
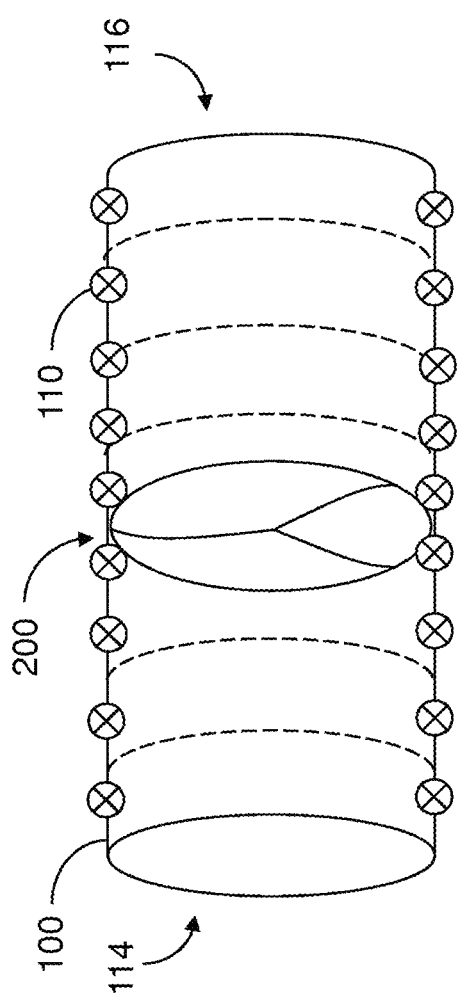
FIG. 9C shows a bendable conduit having a valve in accordance with some embodiments.
Figure 9D:
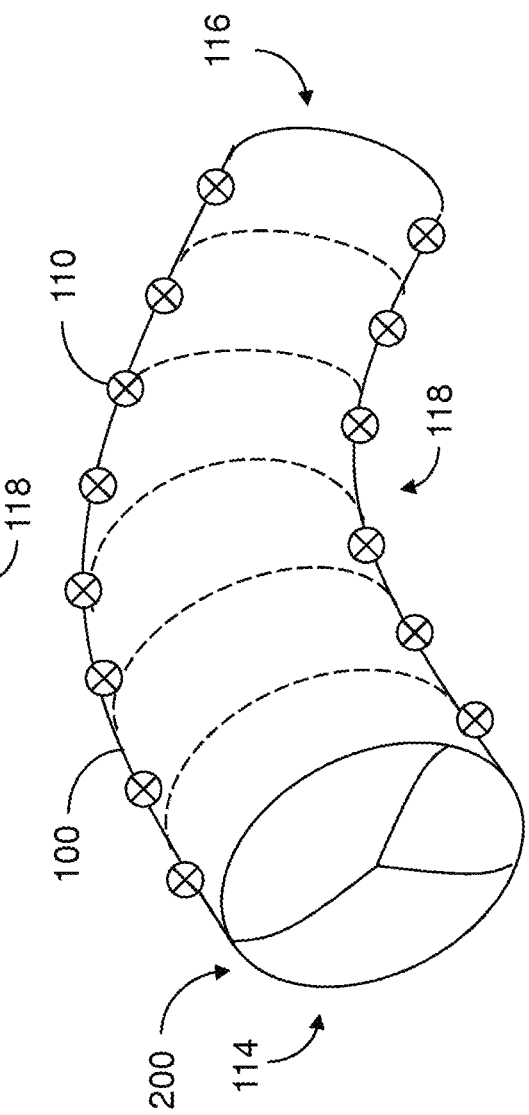
FIG. 9D depicts another bendable conduit having a valve in accordance with some embodiments.

FIGS. 9C and 9D show bendable conduits 100 including a valve 200 located within the lumen of the conduit. Coupling members 110 are disposed at various positions along the exterior surface of each conduit. In the embodiment shown in FIG. 9C, the valve is disposed at a midpoint region 118 of the conduit between opposing ends 114, 116. FIG. 9D depicts the conduit shaped in a curved configuration which may be appropriate during implantation at particular vessel locations within the body. In this instance, the valve 200 may be located at one of the ends 114 or 116, or at a midpoint 118. Such arrangements may be suitably deployed, as discussed previously, in accordance with a transcatheter valve assembly at an appropriate location in the body (e.g., ascending aorta, thoracic aorta, abdominal aorta, other bodily vessels, etc.). The valve may be constructed as part of the conduit. Alternatively, the valve may be deployed within the conduit by any suitable method including that utilized for existing transcatheter valve technology (e.g. stent-mounted valves), or another appropriate technology that provides for the mounting of valves within the conduit. In some cases, the valve may interact with suitable features of the conduit that may be built into the structure for the valve to be mounted therein.

Any suitable bendable conduit may be used for treating a vessel. In some embodiments, devices described herein employ a bendable, aortic valved conduit (e.g., porcine valve) that may be beneficial for repairing the ascending aorta. In some embodiments, a bendable conduit is deployed within a vessel for treating the vessel. In other embodiments, a bendable conduit is employed to replace the vessel entirely. In some embodiments, a bendable conduit is deployed exterior to a vessel and, hence, may serve to mechanically support the tissue of an abnormally enlarged or weakened vessel. In some embodiments, a bendable conduit is provided as a conduit that serves to bypass a particular region of a vessel. The bendable conduit, in general, may have a suitable length and may exhibit an appropriate degree of flexibility.

At various points during deployment and/or after deployment, the conduit may take on an appropriate shape. In some embodiments, the conduit has a diameter at one region that is greater or less than a diameter at another region. For example, upon deployment, a conduit may take on the shape of a hyperboloid where the conduit is constricted at a midpoint region; that is, the diameter of the conduit at the midpoint is less than the diameter of the conduit at opposite ends. Or, in the alternative, when the device is fully deployed, for some cases, the conduit may have a shape that is opposite to a hyperboloid, or somewhat ellipsoid, for example, the conduit may have a diameter at the midpoint that is greater than the diameter of the conduit at opposite ends.

FIGS. 10A-10B depict an illustrative embodiment that includes a conduit 300 having opposing ends 310, 320 where the diameter $d_1$ at the ends 310, 320 is greater than the diameter $d_2$ at a midpoint region 330. In an embodiment, the equilibrium configuration of the conduit 300 upon deployment involves the conduit substantially taking on the shape of a hyperboloid. In some cases, the constricted lumen may provide for fluid flow to be faster through the constricted portion of the conduit at the midpoint region 330 than at the ends 310, 320 of the conduit.

FIG. 11 illustrates a hyperboloid shaped conduit 300 deployed in a vessel 90 where fluid flow, depicted by the solid arrows, travels faster through the midpoint region 330 of the conduit than at the ends 310, 320 of the conduit. Consequently, due to the faster fluid flow at the midpoint region 330 of the conduit, a Venturi effect may arise where the overall pressure due to hydrodynamics is comparatively less at the midpoint region 330 of the conduit than the pressure at the ends 310, 320 of the conduit. In some embodiments, the Venturi effect provided by fluid flow through the conduit 300 results in an inward radial force, depicted by the dashed arrows, exerted on the vessel wall. While not expressly shown in the figures, the conduit may be coupled to the vessel wall via one or more coupling members. Accordingly, the coupling members and the conduit may cooperate in exerting an inward radial force on the vessel wall; that is, the coupling members may couple the conduit and the vessel wall together at a desired location and the conduit may provide a structure that causes formation of a fluid flow profile resulting in the exertion of an inward radial force on the vessel wall.

In some cases, such an inward radial force arising from the pressure variance at different locations of the vessel serves to pull the vessel wall radially inward, in a non-contact manner, toward the conduit. Accordingly, the conduit functions not only to provide a passageway diverting fluid from contacting a diseased region of the vessel, but the conduit also serves to restrain the vessel wall from further dilation. In some instances, the inward radial force provides a degree of relief for the vessel wall, lessening the amount of hydrostatic or hydrodynamic pressure that would otherwise contribute to undesirable dilation of the vessel.

In some embodiments, a conduit having a more restrictive waist at its midpoint may exhibit a gradual transition into and out of the region having the smallest diameter so that the possibility of turbulence arising from fluid flow through the constricted portion is decreased. In some cases, maintaining laminar flow characteristics through the internal lumen of the conduit lessens the overall risk of increasing vessel dilation.

Suitable devices may be structured to employ principles of tensegrity where the conduit includes both rigid and elastic features and materials so that the conduit may be adjustably collapsible and expandable. In some embodiments, a device for treating vessels includes a conduit that behaves as a tensegrity cylinder where the conduit assumes a hyperboloid equilibrium conformation that provides for physical separation between the exterior surface of the conduit and the interior of the vessel wall. FIG. 10 provides an embodiment of this concept. Principles of tensegrity construction and behavior may be applied to various embodiments, concepts and explanations described and illustrated herein. As discussed previously, since fluid flows through the conduit, a spatial separation of fluid flow from the vessel wall may serve to reduce the transfer of hydrostatic or hydrodynamic pressure from the fluid to the vessel.

Tensegrity may generally involve the structural cooperation of a number of support members, for example, with a high aspect ratio, arranged to exhibit an equilibrium state where discrete members in tension and compression assume a natural and predictable conformation when left unconstrained. In some cases, individual support members may take on largely compressive or tensile forces.

In cylindrical form, the precise conformation of a tensegrity structure incorporated in a conduit may depend on the connectivity between tensile and compressive elements. A conduit structured as a tensegrity cylinder may include two ringed ends that have a number of regularly spaced nodes along the circumference of each ringed end. In some embodiments, each node within a ringed end is joined to at least one additional node within that ringed end by a cable or strut (e.g., flexible or rigid strut) oriented within the plane defined by the ringed end. Each ringed end may also be joined to the ringed end on the opposite side of the tensegrity cylinder by a number of longitudinal support members, such as tensile cables or tensile/compressive struts, at respective nodes. Ringed ends may also be joined together by elastic members, such as elastomers. In some embodiments, a longitudinal support member may join corresponding nodes on opposing ringed ends such that the support member runs perpendicular to the ringed end, allowing the conduit to be substantially shaped as a cylinder. In some embodiments, a longitudinal support member may join nodes on opposing ringed ends that are offset one or more nodal spaces from one another such that the longitudinal member forms an angle with respect to the ringed end. In this respect, the overall structure of the conduit may exhibit a twisting motion as the conduit relaxes into an equilibrium state (e.g., taking on a substantially hyperboloid shape). In some embodiments, elastic members are arranged to bring about the twisting motion in the conduit to reach a suitable equilibrium state.

The diameter and rotation of the ringed ends may be controlled in any suitable manner. For instance, ringed ends may be constructed to be continuously or discretely adjustable. In some embodiments, a ringed end employs a screw thread, securing bolt, ratcheting structure, or another suitable method, that tracks and controls the size and/or degree of rotation of the ringed end. In an embodiment, the shape of a conduit structured as a tensegrity cylinder is manually or automatically altered from a substantially cylindrical shape to a hyperboloid shape by rotating one ringed end relative to the other. In some embodiments, ringed ends can be expanded and/or constricted appropriately to accommodate the size of the vessel within which the conduit is deployed. Such a device with adjustable properties by any of the aforementioned or other suitable arrangements may be operated via a catheter mechanism, or via any number of systems external to the body, once the device has been in place. It may be advantageous to have the ability to adjust such a device once it is appropriately deployed so as to optimize its characteristics and a fluid flow profile through the conduit.

In some embodiments, a conduit comprising a tensegrity cylinder is constructed to be collapsible upon itself into a linear structure in a manner that permits the conduit to be delivered to a target vessel (e.g., blood vessel) and subsequently expanded into position, such as through a transcatheter system, or surgically. In some cases, coupling members are situated along longitudinal support members of the conduit and provide physical attachment between the conduit and the vessel upon device deployment. In various embodiments, coupling members that include hooks or barbs may be rotatably inserted into the vessel wall as longitudinal support members suitably twist into an equilibrium configuration.

Longitudinal support members may include a material that exhibits a suitable degree of elasticity, such as but not limited to metal alloys (e.g. nitinol) or rubber compounds. Elasticity characteristics allow longitudinal support members of the device to be oriented along a longitudinal axis of the conduit in a linear configuration. In such a configuration, longitudinal support members are stretched from their equilibrium state to be oriented substantially parallel with the longitudinal axis of the conduit so that the conduit conforms to a generally cylindrical shape. When the conduit is permitted to relax into an equilibrium state, the ringed ends rotate slightly relative to one another causing the longitudinal support members to form an angle with the ringed ends and conform to a generally hyperboloid shape.

Figure 12C:
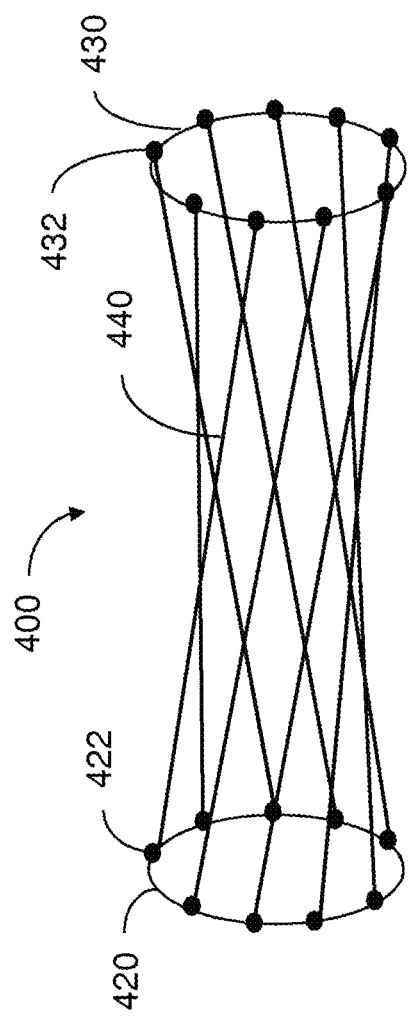

As discussed above, the conduit of an implantable device for treating a vessel includes a number of longitudinal support members (e.g., struts that are able to withstand both tensile and compressive forces, spring-like struts) that contribute to the shape of the conduit and are also configured to alter the overall shape of the conduit when subject to an appropriate stimulus. FIGS. 12A-12C show an illustrative embodiment of a conduit 400 that includes ringed ends 420, 430 having a number of nodes 422, 432 which serve as attachment sites for longitudinal support members 440 (shown as solid lines) and elastic members 450 (shown as dashed lines) disposed between the ends. While not necessary for some embodiments, longitudinal support members are generally arranged parallel to other longitudinal support members. Similarly, elastic members (e.g., elastomers, cables, string, spring-like struts) are arranged to be in parallel with other elastic members, though not necessary for some embodiments. In some embodiments, support members and/or elastic members are provided as spring-like struts, or actual springs, having appropriate degrees of elasticity and strength and that can be suitably deformed or rotated. The support members and elastic members are also configured such that they may be twisted or rotated relative to the ringed ends of the conduit.

FIG. 12A shows a conduit 400 configured to take on a substantially cylindrical shape (for clarity, elastic members 450 are not shown) where longitudinal support members 440 are oriented perpendicular to the ringed ends 420, 430 (parallel to the general direction of fluid flow through the conduit). Each longitudinal support member 440 is attached at nodes on opposing ringed ends that are disposed directly across from one another. FIG. 12B illustrates the conduit including both longitudinal support members 440 and elastic members 450. Elastic members 450 are attached at nodes on opposing ringed ends that are offset with respect to one another. It can be appreciated that elastic members and longitudinal support members may be attached at nodes on opposing ringed ends according to any suitable pattern.

The conduit may alter in shape upon relative rotation of the ringed ends 420, 430. As such, upon rotation of the ringed ends relative to one another, the longitudinal support members enter into a twisted configuration forming an angle less than 90 degrees with the ringed ends and causing the conduit to take on more of a substantially hyperboloid shape.

In some embodiments, the elastic members urge the conduit toward an equilibrium conformation. For example, prior to final deployment, the ringed ends may be held at a certain configuration relative to one another and, when released, the elastic members may cause rotation of the ringed ends into the equilibrium conformation. FIG. 12C depicts the conduit 400 where the ringed ends 420, 430 are rotated slightly with respect to one another into an equilibrium conformation, resulting in twisting of the longitudinal support members 440 so that the conduit forms a slightly hyperboloid shape (for clarity, elastic members 450 are not shown).

In some cases, one or more tensioning elements, such as elastomers, cable, springs or string, are provided around the circumference of the ringed ends between respective nodes providing stability and flexibility in the shape of the conduit. Tensioning elements may connect neighboring nodes along the circumference of a ringed end together and may appropriately contribute to expansion or constriction of the conduit.

When the shape of the conduit is adjusted from a substantially cylindrical conformation to a hyperboloid conformation, the diameter of the conduit at a midpoint region may decrease. In some cases, the diameter at the ends of the conduit may also decrease. In some embodiments, during adjustment of the shape of the conduit, the diameter of the conduit at the midpoint region may decrease more dramatically than the diameter of the conduit at the ends, hence, giving rise to a hyperboloid shape.

Figure 13A:
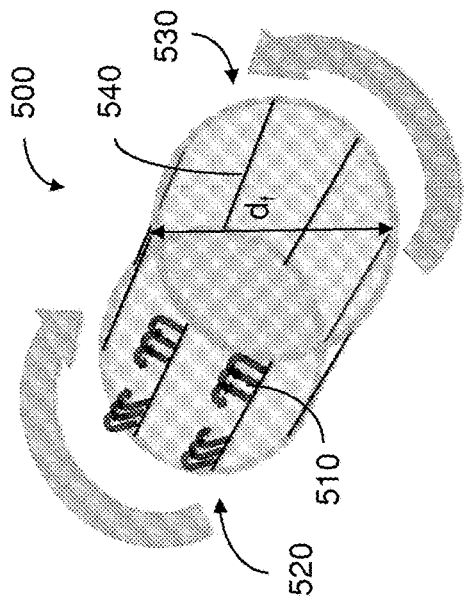
FIGS. 13A-13B illustrate a device in various configurations in accordance with some embodiments.
Figure 13B:
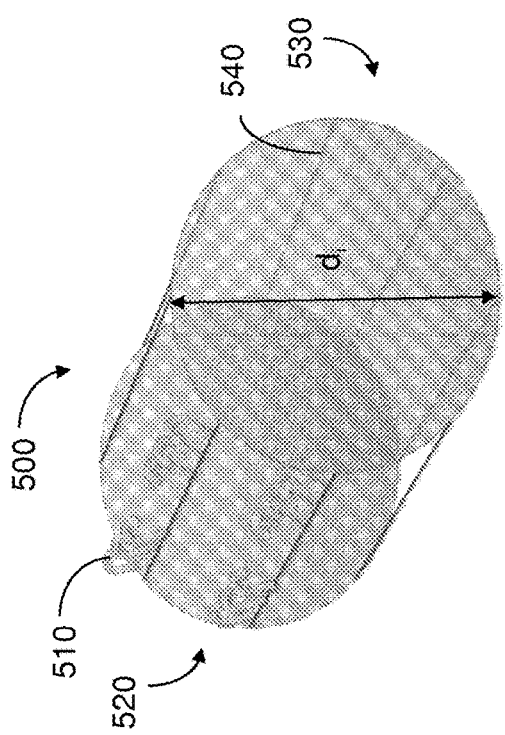

FIG. 13A-13B depict an illustrative embodiment of an implantable device for treating a vessel including a conduit 500 having a number of longitudinal support members 540 and coupling members 510 in the form of hooks disposed along the support members on an exterior surface of the conduit. In FIG. 13A, the conduit is depicted in an expanded configuration, having an initial diameter $d_i$ at the ringed ends 520, 530. In FIG. 13B, the overall conformation of the conduit is adjusted (e.g., ringed ends 520, 530 are rotated with respect to one another) to result in the diameter at the ends 520, 530 decreasing to a final diameter $d_f$. In some embodiments, however, $d_f$ may be equal to $d_i$ at the ringed ends of the device, with a central portion of the conduit typically assuming a smaller diameter as depicted in FIG. 12C. Alternatively, the twisting movement depicted in FIG. 13B may be utilized merely to engage the coupling members with the vessel, as further described below, without substantial contraction of the diameter of the conduit.

Figure 13C:
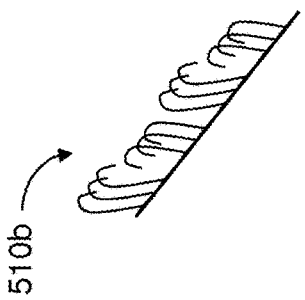
FIGS. 13C-13D depict coupling members of a device in accordance with some embodiments.
Figure 13D:
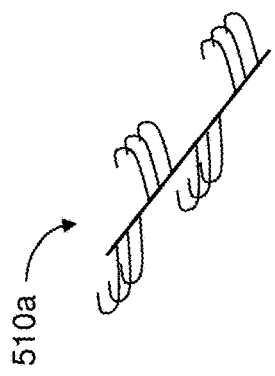

As depicted in FIG. 13C, when the conduit is expanded so that the ringed ends have the initial diameter $d_i$, the coupling members are oriented in an open configuration 510a such that the coupling members are readily engageable with a vessel wall. For instance, in an open configuration, a hooked coupling member may be positioned such that a sharp end of the hook faces outward toward the vessel wall or in an orientation that allows for ready engagement with the vessel wall. After coupling of the conduit and the vessel wall, the conduit constricts to an equilibrium conformation where the ringed ends exhibit a final diameter $d_f$. As a result, the coupling members are retracted into a closed configuration 510b (e.g., oriented to face inward in a manner that sets the hooks firmly to the vessel wall), as shown in FIG. 13D, so as to firmly secure the conduit and the vessel wall together. As discussed above, the final diameter $d_f$ is not required to be substantially smaller than the natural diameter of the vessel prior to intervention, or substantially smaller than the initial diameter $d_i$ of the device before deployment.

So as to accommodate a variety of applications, implantable devices described herein may be highly flexible and may be used in bodily vessels other than blood vessels such as, for example, an internal flow restrictor, a pulmonary artery band or an artificial sphincter. It can be appreciated that devices in accordance with the present disclosure may be used for a number of medical or non-medical applications. In some embodiments, implantable devices described herein may function as an artificial sphincter to restrict flow through a vessel, such as through a segment of intestine or a urethra. In an embodiment, an implantable device is used as a flow restrictor of a blood vessel, such as for use in the pulmonary artery, other native vessels and/or surgically created shunts and conduits. Non-medical applications may include the incorporation of an adjustable, centrally constricted conduit such as that described above for the purposes of flow modulation within various industrial or laboratory instruments. Such an arrangement may allow for continuously adjustable fluid flow with reduced turbulence, due to the geometric features of the conduit. For example, a device that employs the above described tensegrity principles may be employed as an artificial sphincter or industrial low-turbulence flow regulator. Suitable embodiments described may be incorporated within the structure of a non-bodily vessel, such as a pipe, and can be manipulated to constrict the lumen of the vessel.

Suitable implantable devices may be placed internal to a vessel or, in some cases, implantable devices in accordance with some embodiments may be placed exterior to (e.g., surrounding) a vessel. In some embodiments, a suitable implantable device may be placed endoluminally (e.g. endovascularly) or circumferentially around the vessel. An artificial sphincter may be deployed and mounted within or external to a bodily vessel, such as an intestine which may be opened/closed automatically or manually via any number of systems including, but not limited to those described above, to control passage of fluid or material through the vessel.

In some embodiments, the device includes drug-eluting features. For example, the conduit and/or coupling members may include materials that function to deliver appropriate bioactive agents for exposure of the agent and treatment a particular region.

Embodiments described may be for use as an improvement of the Melody Transcatheter Pulmonary Valve, manufactured by Medtronic, Inc., the BioValsalva valved conduit, manufactured by Grupo Cardiva, or the St. Jude Medical Masters Valved Graft. Such improvements may include the ability to deliver a conduit by catheter-directed methods, rather than surgically. However, it should be appreciated that features of the present disclosure may be used in any suitable arrangement for treating a vessel. In some cases, valve conduits described may be used to provide a fluid passageway between any appropriate regions, such as for example, between ends of a resected bodily vessel, cavities and/or channels within the body.

The above aspects may be employed in any suitable combination as the present invention is not limited in this respect. Also, any or all of the above aspects may be employed in a valve arrangement; however, the present invention is not limited in this respect, as aspects of the invention may be employed with other medical devices.

Having thus described several aspects of at least one embodiment of this invention, it is to be appreciated various alterations, modifications, and improvements will readily occur to those skilled in the art. For example, the prosthesis described herein may be adapted for placement in other locations. In some embodiments, as discussed above, a prosthesis described herein may include material that is radioopaque so that suitable imaging may occur. Such alterations, modification, and improvements are intended to be part of this disclosure, and are intended to be within the spirit and scope of the invention. Accordingly, the foregoing description and drawings are by way of example only.

What is claimed is:

1. An implantable device for a vessel, the device comprising:
   a conduit; and
   at least one coupling member disposed on the conduit and arranged to couple a portion of the conduit with a wall region of the vessel at an interior of the vessel, the at least one coupling member cooperating with the conduit to exert an inward radial force on the wall region of the vessel.

2. The implantable device of claim 1, further comprising at least one coupling device located at a midpoint region of the conduit between a first end portion and a second end portion of the conduit.

3. The implantable device of claim 1, further comprising a membrane attached to the conduit for reducing leakage of fluid between an interior region and an exterior region of the conduit.

4. The implantable device of claim 3, wherein the membrane covers the conduit.

5. The implantable device of claim 1, wherein the conduit comprises a substantially hyperboloid shape.

6. The implantable device of claim 1, wherein the at least one coupling member comprises a first coupling device located at a first end portion of the conduit and a second coupling device located at a second end portion of the conduit.

7. The implantable device of claim 1, wherein the conduit is constructed and arranged to be implanted at an abdominal aorta region, an aortic arch region, or a descending thoracic aorta region.

8. The implantable device of claim 1, further comprising a valve disposed within a lumen of the conduit.

9. The implantable device of claim 1, wherein, upon coupling of the portion of the conduit and the wall region of the vessel, a barrier to fluid flow is formed between the coupled portion of the conduit and the wall region of the vessel.

10. The implantable device of claim 9, wherein the barrier to fluid flow comprises a seal between the portion of the conduit and the wall region of the vessel.

11. The implantable device of claim 10, wherein the seal comprises a sealing material disposed between the portion of the conduit and the wall region of the vessel.

12. The implantable device of claim 1, wherein the conduit comprises a stent.

13. The implantable device of claim 12, wherein the stent is constructed and arranged to alter in shape upon rotation of the first end portion relative to the second end portion of the conduit.

14. The implantable device of claim 13, wherein the shape comprises an exterior surface of the conduit spaced inward from an interior surface of the vessel.

15. The implantable device of claim 1, further comprising at least one tensioning element coupled to at least one of the first end portion or the second end portion of the conduit.

16. The implantable device of claim 1, wherein the conduit is constructed and arranged to comprise a diameter when deployed in the vessel that is less than a diameter of the vessel when the conduit is not deployed in the vessel.

17. The implantable device of claim 1, wherein, upon deployment, the conduit is constructed and arranged to decrease or maintain a diameter of the vessel.

18. The implantable device of claim 1, wherein the conduit is constructed and arranged to comprise a diameter in a deployed configuration of between about 2 cm and about 5 cm.

19. A method of treating a vessel, comprising:
   implanting a device having a conduit within the vessel,
   coupling a portion of the conduit with a wall region at an interior of the vessel via at least one coupling member; and
   exerting an inward radial force on the wall region of the vessel via at least one of the conduit and the at least one coupling member at the coupled portion of the conduit.

20. An implantable device for a vessel, the device comprising:
   a conduit having a midpoint region located between a first end portion and a second end portion of the conduit; and
   at least one coupling member arranged to couple at least the midpoint region of the conduit with a wall region of the vessel at an interior of the vessel;
   wherein the at least one coupling member cooperates with the conduit to exert an inward radial force on the wall region of the vessel.

21. The implantable device of claim 1, wherein the at least one coupling member includes at least one hook, barb, adhesive material, staple, or suture.

22. The implantable device of claim 1, wherein the at least one coupling member cooperates with the conduit to pull the wall region of the vessel radially inward.

23. The implantable device of claim 22, wherein, when the implantable device is deployed, a diameter of the conduit is constricted and the at least one coupling member pulls the wall region of the vessel radially inward.

* * * * *